(12) United States Patent
Brainard

(10) Patent No.: US 8,501,382 B1
(45) Date of Patent: Aug. 6, 2013

(54) ACID AMPLIFIERS

(75) Inventor: Robert L. Brainard, Albany, NY (US)

(73) Assignee: The Research Foundation of State Univ. of New York, Albany, NY (US)

( * ) Notice: Subject to any disclaimer, the term of this patent is extended or adjusted under 35 U.S.C. 154(b) by 430 days.

(21) Appl. No.: 12/708,958

(22) Filed: Feb. 19, 2010

Related U.S. Application Data

(60) Provisional application No. 61/154,112, filed on Feb. 20, 2009.

(51) Int. Cl.
*G03F 7/004* (2006.01)
*G03F 7/039* (2006.01)
*G03F 7/20* (2006.01)
*C07C 309/65* (2006.01)
*C07C 309/72* (2006.01)

(52) U.S. Cl.
USPC ............ 430/270.1; 430/272.1; 430/311; 430/325; 430/326; 430/919; 430/920; 430/921; 430/922; 430/925; 430/942; 558/51; 558/44; 558/48; 558/49; 558/52; 558/53; 558/54; 558/56; 558/57; 558/58; 526/287; 526/288

(58) Field of Classification Search
None
See application file for complete search history.

(56) References Cited

U.S. PATENT DOCUMENTS

| 5,128,264 | A | * | 7/1992 | Sih ........................ 435/280 |
| 2011/0127651 | A1 | | 6/2011 | Brainard et al. |
| 2011/0130538 | A1 | | 6/2011 | Brainard et al. |
| 2011/0152496 | A1 | | 6/2011 | Brainard et al. |

OTHER PUBLICATIONS

Brainard et al ("Lithographic Evaluation and Chemical Modeling of Acid Amplifiers used in EUV Photoresists", Proceedings of SPIE, vol. 7273, p. 72733Q-1-72733Q-10 (Apr. 1, 2009).*

* cited by examiner

*Primary Examiner* — Sin J. Lee
(74) *Attorney, Agent, or Firm* — Heslin Rothenberg Farley & Mesiti P.C.

(57) ABSTRACT

There are disclosed sulfonic acid precursor compositions, as are methods of using these compositions in, for example, photolithography. Other embodiments are also disclosed.

27 Claims, No Drawings

ACID AMPLIFIERS

CROSS-REFERENCE TO RELATED APPLICATIONS

This application claims benefit from U.S. Provisional Application 61/154,112, filed Feb. 20, 2009. The entire contents of the prior application are incorporated herein by reference.

FIELD OF THE INVENTION

The invention relates to compositions and methods for acid amplification in photoresists and other relevant applications.

BACKGROUND

Photolithography or optical lithography is a process used, inter alia, in semiconductor device fabrication to transfer a pattern from a photomask (sometimes called reticle) to the surface of a substrate. Such substrates are well known in the art. For example, silicon, silicon dioxide and aluminum-aluminum oxide microelectronic wafers have been employed as substrates. Gallium arsenide, ceramic, quartz and copper substrates are also known. The substrate often includes a metal coating.

Photolithography generally involves a combination of substrate preparation, photoresist application and soft-baking, radiation exposure, development, etching and various other chemical treatments (such as application of thinning agents, edge-bead removal etc.) in repeated steps on an initially flat substrate. In some more recently-developed techniques, a hard-bake step is implemented after exposure and prior to development.

A cycle of a typical silicon lithography procedure begins by applying a layer of photoresist—a material that undergoes a chemical transformation when exposed to radiation (generally but not necessarily visible light, ultraviolet light, electron beam, or ion beam)—to the top of the substrate and drying the photoresist material in place, a step often referred to as "soft baking" the photoresist, since typically this step is intended to eliminate residual solvents. A transparent plate, called a photomask or shadowmask, which has printed on it areas that are opaque to the radiation to be used as well as areas that are transparent to the radiation, is placed between a radiation source and the layer of photoresist. Those portions of the photoresist layer not covered by the opaque areas of the photomask are then exposed to radiation from the radiation source. Exposure is followed by development. In some cases, exposure is followed by a post-exposure bake (PEB), which precedes the development. Development is a process in which the entire photoresist layer is chemically treated. During development, the exposed and unexposed areas of photoresist undergo different chemical changes, so that one set of areas is removed and the other remains on the substrate. After development, those areas of the top layer of the substrate which are uncovered as a result of the development step are etched away. Finally, the remaining photoresist is removed by an etch or strip process, leaving exposed substrate. When a "positive" photoresist is used, the opaque areas of the photomask correspond to the areas where photoresist will remain upon developing (and hence where the topmost layer of the substrate, such as a layer of conducting metal, will remain at the end of the cycle). "Negative" photoresists result in the opposite—any area that is exposed to radiation will remain after developing, and the masked areas that are not exposed to radiation will be removed upon developing.

The need to make circuits physically smaller has steadily progressed over time, necessitating inter alia the use of light of increasingly shorter wavelengths to enable the formation of these smaller circuits. This in turn has necessitated changes in the materials used as photoresists, since in order to be useful as a photoresist, the material should not absorb light at the wavelength used. For example, phenolic materials which are commonly used for photolithography using light of wavelength 248 nm wavelength are generally not suitable for use as photoresists for light of 193 nm, since these phenolic materials tend to absorb 193 nm light.

At present, it is desired to use light in the extreme UV range (13.5 nm or shorter) for photolithography of circuits having line widths of 32-20 nm. Many of the materials which would be suitable for use as positive photoresists in this range are polymers which contain acidic groups in protected form, such as tert-butoxycarbonyl (t-BOC) protected forms of polymers derived from polyhydroxystyrene or t-butylacrylate polymers. Following the "soft bake" of the photoresist, exposure of the masked photoresist to radiation and, if necessary, post-exposure bake should result in deprotection of polymers in the areas which were not covered by the opaque portions of the mask, thus rendering these areas susceptible to attack by base, to enable the removal of these areas in the development step. In order to achieve this result, it has been proposed to utilize "chemically amplified" photoresists. The idea is to include in the photoresist an amount of a thermally stable, photolytically activated acid precursor (sometimes called a "photoacid generator" or "PAG"), so that upon irradition acid will be generated which can deprotect the irradiated portions of the positive photoresist polymer, rendering them susceptible to base attack.

In a variation on the chemical amplification technique, it has been proposed to include in the resist composition a photoacid generator, as well as an acid precursor (sometimes referred to as an "acid amplifier") which is (a) photolytically stable and (b) thermally stable in the absence of acid but thermally active in the presence of acid. In such systems, during radiation exposure the PAG generates acid, which then during post-exposure bake acts as a catalyst to activate the acid-amplifier. Such systems are sometimes referred to in the literature as "acid amplifier" systems, since the catalytic action of the photolytically-generated acid on the second acid precursor during post-exposure bake results in an effective number of acid molecules which is higher than the number of photons absorbed during radiation exposure, thus effectively "amplifying" the effect of exposure and amplifying the amount of acid present.

Similarly, the use of PAGs and acid amplifiers in negative resists has been proposed. In these cases, the acid generated makes the areas of resist exposed to radiation less soluble in the developing solvent, usually by either effecting or catalyzing cross-linking of the resist in the exposed areas or by changing the polarity or hydrophilicity/hydrophobicity in the radiation-exposed areas of the resist.

Among the difficulties encountered in trying to implement chemical amplification photoresists systems is "outgassing", a process whereby, as a result of acid formation, gas is generated, leading to volatile compounds that can leave the resist film while the wafer is still in the exposure tool. Outgassing can occur under ambient conditions or under vacuum as is used with extreme ultraviolet (EUV) lithography. Outgassing is a problem because the small molecules can deposit on the optics (lenses or mirrors) of the exposure tool and cause a diminution of performance. Furthermore, there is a trade-off between resolution, line-width roughness and sensitivity. A resist's resolution is typically characterized as the smallest feature the resist can print. Line width roughness is the statistical variation in the width of a line. Sensitivity is the dose of radiation required to print a specific feature on the resist, and is usually expressed in units of mJ/cm². Moreover, hitherto it has proven difficult to find acid precursors which display the requisite photostability, thermal stability in the absence of acid, and thermal acid-generating ability in the presence of acid, and which generate acids which are sufficiently strong so as to deprotect the protected resins used in photolithography.

Thus, although some acid amplifier systems have been proposed for use in photolithography using 248 nm light, there remains a need for acid amplifier systems which may be used in photolithography, particularly for use in extreme UV (13.5 nm) or electron-beam lithography.

BRIEF DESCRIPTION OF THE INVENTION

In one aspect the invention relates to a photoresist composition that includes a sulfonic acid precursor. The sulfonic acid precursor, in the presence of an acid, is capable of autocatalytically generating a sulfonic acid. In some embodiments, the sulfonic acid precursor is of formula I:

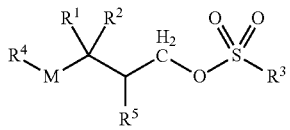

wherein
M is —O—, —S— or —NR$^9$—;
R$^1$ is chosen from (C$_1$-C$_8$) saturated hydrocarbon; (C$_1$-C$_8$) saturated hydrocarbon substituted with halogen, cyano or nitro; (C$_1$-C$_8$) silaalkane and optionally substituted phenyl;
R$^2$ is chosen from H, (C$_1$-C$_6$) hydrocarbon and (C$_1$-C$_6$) hydrocarbon substituted with nitro or cyano, or taken together with the carbon to which they are attached, R$^1$ and R$^2$ form a (C$_4$-C$_6$) hydrocarbon ring;
R$^3$ is chosen from
 (a) —C$_n$H$_m$F$_p$ wherein n is 1-8, m is 0-17, p is 0-17 and the sum of m plus p is 2n+1;
 (b) —CH$_2$C(=O)-Q;
 (c) —CF$_2$C(=O)-Q;
 (d)

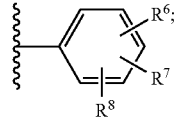

(e) —(CH$_2$)$_q$Cl, wherein q is an integer from 1 to 8;
R$^4$ is chosen from H, (C$_1$-C$_6$)alkyl, —C(=O)(C$_1$-C$_6$)alkyl, —C(=O)(C$_1$-C$_6$)alkenyl, —C(=O)(C$_1$-C$_6$)haloalkyl, benzyl, substituted benzyl, —C(=O)phenyl, —C(=O)substituted phenyl, —SO$_2$-phenyl and —SO$_2$ (substituted)phenyl;
R$^5$ is chosen from H, (C$_1$-C$_6$) hydrocarbon, nitro, cyano, (C$_1$-C$_6$) hydrocarbon substituted with nitro or cyano, and (C$_1$-C$_6$)silaalkane, or together with the carbons to which they are attached, R$^1$ and R$^5$ form a (C$_4$-C$_6$) hydrocarbon ring;
R$^6$ is chosen from H, CH$_3$, —CF$_3$, —OCH$_3$, —NO$_2$, F, Br, Cl, —CH$_2$Br, —CH=CH$_2$, —OCH$_2$CH$_2$Br, —CH$_2$-Q, —O-Q, —OCH$_2$CH$_2$-Q, —OCH$_2$CH$_2$O-Q and —CH(Q)CH$_2$-Q;
R$^7$ is chosen from one to three instances of H, —CF$_3$, —OCH$_3$, —CH$_3$, —NO$_2$, F, Br, and Cl;
R$^8$ is chosen from H, —CF$_3$, —OCH$_3$, —CH$_3$, —NO$_2$, F, Br, and Cl;

R$^9$ is chosen from H, (C$_1$-C$_6$)alkyl, —C(=O)(C$_1$-C$_6$)alkyl and phenyl, or taken together with R$^4$, R$^9$ together with the nitrogen to which they are attached may form a nitrogen heterocycle, with the proviso that one of R$^4$ and R$^9$ must be an acyl, and when R$^4$ and R$^9$ together with the nitrogen to which they are attached form a heterocycle, the heterocycle must contain one or two α-oxo substituents; and
Q is a polymer or oligomer.

In other embodiments the sulfonic acid precursor in the photoresist composition is of formula:

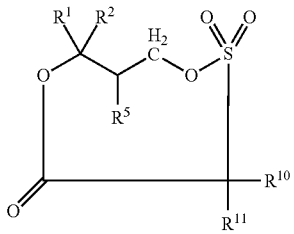

wherein R$^{10}$ is chosen from H, F and (C$_1$-C$_6$) hydrocarbon; and R$^{11}$ is chosen from H and F.

In other embodiments the sulfonic acid precursor in the photoresist composition is of formula:

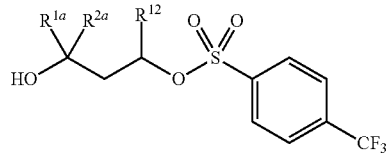

wherein
R$^{1a}$, and R$^{12}$ are independently chosen from (C$_1$-C$_8$)saturated hydrocarbon; and
R$^{2a}$ is chosen from H and (C$_1$-C$_6$) hydrocarbon.

All of the compounds falling within the foregoing three parent genera and their subgenera are useful for photolithography. It may be found upon examination that compounds that have been included in the claims are not patentable to the inventors in this application. In this event, subsequent exclusions of species from the compass of applicants' claims are to be considered artifacts of patent prosecution and not reflective of the inventors' concept or description of their invention; the invention encompasses all of the members of the three genera described above that are not already in the possession of the public. The invention also encompasses the use of a broader genus of compounds in photoresists.

Most, but not all, of the acid amplifiers disclosed herein are novel, and thus, there are provided in some embodiments of the invention, the molecules per se, as well as methods for preparing these molecules. In this aspect the invention relates to compounds of formula

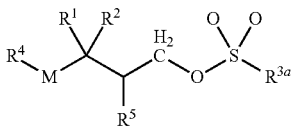

wherein
R$^{3a}$ is chosen from
 (a) —C$_n$H$_m$F$_p$ wherein n is 2-8, m is 0-16, p is 1-17 and the sum of m plus p is 2n+1;
 (b) —CH$_2$C(=O)-Q;

(c) —$CF_2C(=O)$-Q;

(d)

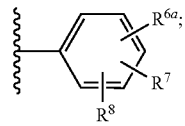

(e) —$(CH_2)_qCl$, wherein q is an integer from 1 to 8;

(f) when none of $R^1$, $R^2$ and $R^5$ contains or forms a carbocycle, $R^3$ may additionally be

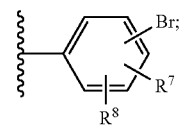

and $R^{6a}$ is chosen from —$CF_3$, —$OCH_3$, —$NO_2$, F, Cl, —$CH_2Br$, —$CH=CH_2$, —$OCH_2CH_2Br$, —$CH_2$-Q, —O-Q, —$OCH_2CH_2$-Q, —$OCH_2CH_2O$-Q, and —$CH(Q)CH_2$-Q.

In some embodiments, the photoresist composition is suitable for preparing a positive photoresist. In some embodiments, the photoresist composition is suitable for preparing a negative photoresist. In some embodiments, the photoresist composition is suitable for preparing a photoresist using 248 nm, 193 nm, 13.5 nm light, or using electron-beam or ion-beam radiation.

There is also provided, in accordance with some embodiments of the invention, a photoresist substrate which is coated with a photoresist composition in accordance with embodiments of the invention. In some embodiments, the photoresist substrate comprises a conducting layer upon which the photoresist composition is coated.

There is also provided, in accordance with embodiments of the invention, a method for preparing a substrate for photolithography, comprising coating said substrate with a photoresist composition according to embodiments of the invention.

There is also provided, in accordance with embodiments of the invention, a method for etching conducting photolithography on a substrate, comprising (a) providing a substrate, (b) coating said substrate with a photoresist composition according to embodiments of the invention, and (c) irradiating the coated substrate through a photomask.

In some embodiments, the process of coating comprises applying the photoresist composition to the substrate and baking the applied photoresist composition on the substrate.

In some embodiments, the irradiating is conducted using radiation of sufficient energy and for a sufficient duration to effect the generation of acid in the portions of the photoresist composition which has been coated on said substrate which are exposed to the radiation.

In some embodiments, the method further comprises (e) after the irradiating but before the developing, baking the coated substrate. In some embodiments, the baking is conducted at a temperature and for a time sufficient for the sulfonic acid precursor in the photoresist coating to generate sulfonic acid.

DETAILED DESCRIPTION

Substituents $R''$ are generally defined when introduced and retain that definition throughout the specification and in all independent claims.

The invention relates to compounds of formulae

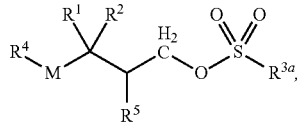

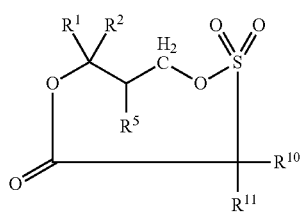

and

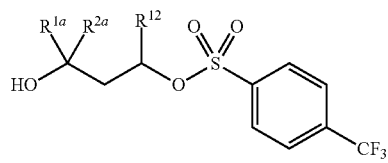

In certain embodiments, $R^{3a}$ is —$C_nF_{2n+1}$. In other embodiments $R^{3a}$ is

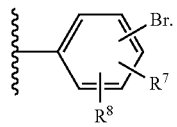

In other embodiments, $R^{3a}$ is

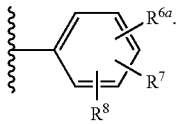

In these embodiments, $R^{6a}$ may be $CF_3$ or $R^{6a}$ may be chosen from —$CH_2Br$, —$CH=CH_2$, and —$OCH_2CH_2Br$. The compounds in which $R^{6a}$ is —$CH_2Br$, —$CH=CH_2$, or —$OCH_2CH_2Br$ are particularly useful as intermediates in the synthesis of compounds wherein $R^{6a}$ is chosen from —$CH_2$-Q, —O-Q, —$OCH_2CH_2$-Q, —$OCH_2CH_2O$-Q and —$CH(Q)CH_2$-Q.

In certain embodiments, $R^1$ is chosen from methyl, propenyl, propynyl, dimethylbutynyl, cyclopropyl, trimethylsilylmethyl, phenyl, nitrophenyl, nitromethyl, cyanomethyl; and $R^2$ is chosen from H and methyl. In other embodiments, $R^1$ and $R^2$ taken together form a cyclobuty, cyclopentyl or cyclohexyl ring.

In certain embodiments, $R^5$ is chosen from H, $NO_2$, CN, $SiMe_3$, and methyl. In other embodiments, $R^1$ and $R^5$ taken together form a cyclopentyl or cyclohexyl ring.

In certain embodiments, M is oxygen.

In certain embodiments, $R^4$ is chosen from H, methyl, ethyl, isopropyl, t-butyl, benzyl, acetyl, chloroacetyl, dichloroacetyl, trichloroacetyl, benzoyl, 4-(trifluoromethyl)benzoyl, 4-nitrobenzoyl, 4-carboxybenzoyl, 4-methoxybenzoyl, benzenesulfonyl, 4-(trifluoromethyl)benzenesulfonyl, 4-nitrobenzenesulfonyl, 4-carboxybenzenesulfonyl and 4-methoxybenzenesulfonyl.

In certain embodiments, M is —$NR^9$—. In these embodiments, $R^4$ may be chosen from H, methyl, ethyl, isopropyl, t-butyl and benzyl. Alternatively, $R^9$ may be acetyl. In other embodiments, $R^4$, $R^9$ together with the nitrogen to which they are attached form a pyrrolidone, phthalimide, maleimide or succinimide ring.

In certain embodiments, M is sulfur and $R^4$ is chosen from H, methyl, ethyl, isopropyl, t-butyl, benzyl, acetyl, chloroacetyl, dichloroacetyl, trichloroacetyl, benzoyl, 4-(trifluoromethyl)benzoyl, 4-nitrobenzoyl, 4-carboxybenzoyl and 4-methoxybenzoyl.

In certain embodiments, all of $R^{1a}$, $R^{2a}$ and $R^{12}$ are methyl.

In the context of the present application, alkyl is intended to include linear, branched, or cyclic saturated hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. The term "carbocycle" is intended to include ring systems consisting entirely of carbon but of any oxidation state. Thus ($C_3$-$C_{10}$) carbocycle refers to such systems as cyclopropane, benzene and cyclohexene; ($C_8$-$C_{12}$) carbopolycycle refers to such systems as norbornane, decalin, indane and naphthalene.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons (and their associated hydrogens) have been replaced by oxygen. Examples include methoxy, methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquino line, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquino line, tetrahydroisoquino line, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpho-linylsulfone, oxadiazolyl, triazolyl and tetrahydroquinolinyl. An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], cyano, acetoxy, nitro, mercapto, alkylthio, alkylsulfinyl, alkylsulfonyl, aryl, benzyl, oxaalkyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl, cycloalkyl and aryl, more than three hydrogen atoms can be replaced by fluorine; indeed, all available hydrogen atoms could be replaced by fluorine.

The term "halogen" means fluorine, chlorine, bromine or iodine.

Some of the compounds described herein contain one or more asymmetric centers and may thus give rise to enantiomers, diastereomers, and other stereoisomeric forms that may be defined, in terms of absolute stereochemistry, as (R)- or (S)-. Unless indicated otherwise, the present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion.

Terminology related to "protecting", "deprotecting" and "protected" functionalities occurs in some places in this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

The following abbreviations and terms have the indicated meanings throughout:
Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Et=ethyl
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
Ms=mesyl
MTBE=methyl t-butyl ether
NMO=N-methylmorpholine oxide
—OTf=triflate=trifluoromethanesulfonate=—$OSO_2CF_3$
PEG=polyethylene glycol
Ph or κ=phenyl
PhOH=phenol
PfP=pentafluorophenol
PPTS=pyridinium p-toluenesulfonate
PyBroP=bromo-tris-pyrrolidino-phosphonium hexafluorophosphate
rt=room temperature
sat'd=saturated
s-=secondary
t-=tertiary
TBDMS=t-butyldimethylsilyl
-Tf=trifyl=trifluoromethyl sulfonyl=—$SO_2CF_3$
triflate=-OTf=—$OSO_2CF_3$
TFA=trifluoroacetic acid
$T_g$=glass transition temperature
THF=tetrahydrofuran
TMOF=trimethyl orthoformate
TMS=trimethylsilyl
tosyl=Ts=p-toluenesulfonyl=—$SO_2$-para-$(C_6H_4)$—$CH_3$
tosylate=-OTs=—$OSO_2$-para-$(C_6H_4)$—$CH_3$
Trt=triphenylmethyl A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

References herein to acid strengths or, equivalently, $pK_a$ values, particularly with respect to sulfonic and/or photolytically generated acids, refer to values determined by Taft parameter analysis, as such analysis is known in the art and described for example in J. Cameron et al., "Structural Effects of Photoacid Generators on Deep UV Resist Performance," Society of Plastic Engineers, Inc. Proceedings., "Photopolymers, Principles, Processes and Mateials", 11th International Conference, pp. 120-139 (1997) and J. P. Gutthrie, Can. J. Chem., 56:2342-2354 (1978). As reported in U.S. Pat. No. 6,803,169, HOTs (paratoluene sulfonic acid) has a $pK_a$ of −2.66 as determined by Taft parameter analysis. Thus, an acid which is at least as strong as HOTs will have a $pK_a$ of −2.66 or lower, as determined by Taft parameter analysis.

As used herein, the term "sulfonic acid precursor" refers to a molecule which can be decomposed in acidic conditions to generate $HOSO_2R^3$.

As used herein, the term "photoresist polymer" refers to a polymer which may serve as the primary component in a photoresist.

As used herein, the term "photoresist substrate" refers to an article, such as a silicon wafer, which is suitable for use as a substrate in photolithography or other similar processes, and thus may have a photoresist applied thereto as part of the photolithography process.

As used herein, the term "photoresist composition" refers to a composition which may be used in connection with photolithography.

Throughout this application, various patent and non-patent publications are referred to. The disclosures of these publications in their entireties are hereby incorporated by reference as if written herein.

As is known in the art, ESCAP (Environmentaly Stable Chemically Amplified Photoresist) polymers undergo well-known acid catalysis reactions, as shown in Scheme. 1. A central feature of these chemical systems is that the acidolysis reactions only occur in the presence of acid, i.e. catalytically, and they do not occur thermally without acid, except at temperatures ~50° C. above normal post-exposure bake temperatures used in integrated circuit fabrication, i.e at temperatures of approximately 65-140° C. Other types of chemically amplified resists (often called low activation energy resists) can use lower post-exposure temperatures of approximately 20-120 C.

Scheme 1

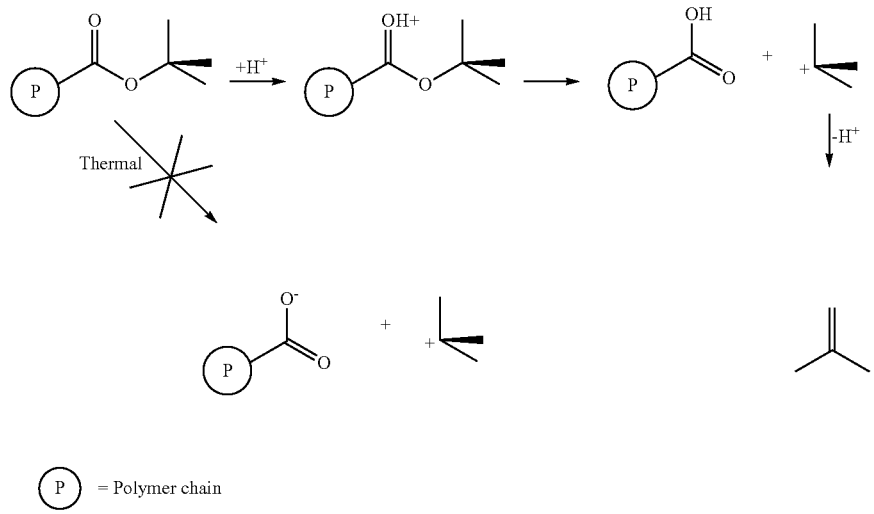

P = Polymer chain

To approximate the thermodynamics of the reaction shown in Scheme 1, the thermodynamics of the reaction shown in Scheme 2, in which t-butyl acetate was used as a simple model for the t-butyl acrylate monomer, were analyzed using Chem3D modeling software from Cambridge Software, and the kinetics of the reaction were modeled using Spartan modeling software. The modeling software was programmed to simulate the thermal and acid catalyzed cleavage of the tertiary carbon and the acetate oxygen by stretching the C—O bond in 18 steps from 1.43 to 2.93 Å. At each step, equilibrium geometries were determined ($\Delta H$) using the semiempirical PM3 method. For the acid catalyzed reaction, the simulation was run with a proton from triflic acid on the sp2 acrylate oxygen. The enthalpic contributions from the additional reactant (triflic acid) and product (triflate anion) during the protonation reaction were tracked. The heat of formation can be determined for each compound (starting material, products, intermediates, using the PM3 potential function in Chem3D. In the these calculations, a dielectric constant of 7 was chosen to approximate the phenolic polymer environment, since this value is intermediate between the dielectric constant of phenol ($\in=10$) and the value favored by Tagawa et al. ($\in=4$), as reported in SPIE (2005), 5753, 361-367 and Journal of Photopolymer Science and Technology (2005), 18(4), 471-474. To simplify calculations, the heat of formation of the starting material, t-butylacetate, was set to zero, i.e. the t-butylacetate was used to define the enthalpic ground state $\Delta H=0$. The relative heat of formation ($\Delta\Delta H$) of each molecule, as calculated, is shown in Scheme 2, in which it can be seen that the acid catalyzed pathway (+28 kcal/mol) is more favorable than the thermal reaction pathway (45 kcal/mol). The homolytic C—O bond cleavage reaction is even less favored than the heterolytic C—O bond cleavage reaction: the enthalpies of these two reactions are +44 and +66 kcal/mole respectively.

Scheme 2.

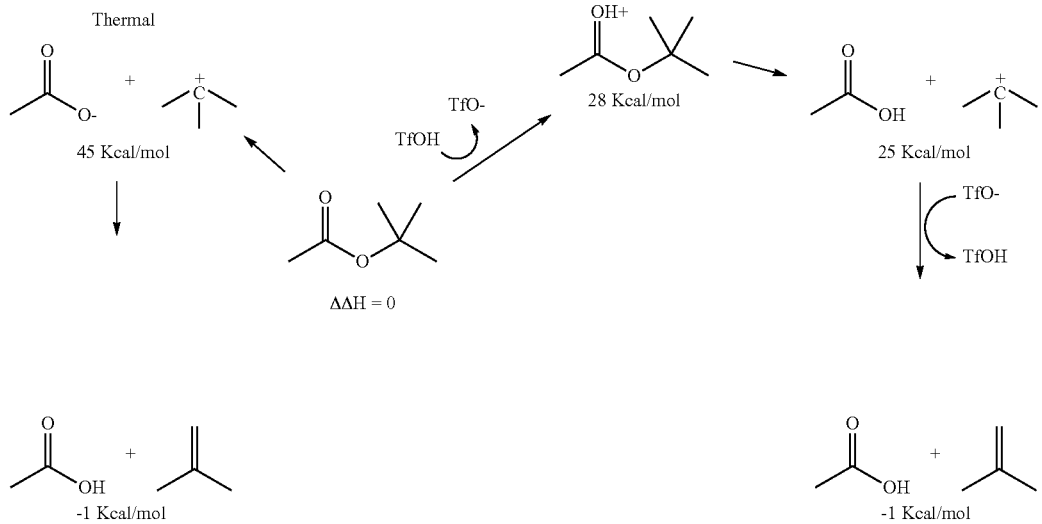

Scheme 3 shows that the catalyzed reaction has a significantly more favored transition state than that of the thermal reaction ($\Delta E_a$=14 kcal/mol). The energies of the two transition states are compared by assuming that the pre-exponential factors ($\Delta_{cat}$, $\Delta_{therm}$) were the same and by assuming that the temperature was 130° C. as a way to estimate the relative rates of these two reaction pathways (catalytic vs. thermal). For this reaction, the ratio of rates ($k_{cat}/k_{therm}$) was estimated to be $1.5 \times 10^8$ or $\log(k_{cat}/k_{therm})$=8.2.

As shown in Scheme 3, similar analysis of the analogous reactions involving t-butyltriflate (thermolytic versus triflic acid-catalyzed decomposition of t-butyltriflate) shows that protonation of the sulfoxide should be very unfavorable (+39 kcal/mol), and that the bond cleavage intermediates both have the same enthalpy of 19 kcal/mole relative to the starting material. This analysis therefore predicts that t-butyltriflate would be a poor acid amplifier, because the uncatalyzed reaction would occur as fast or faster than the catalyzed reaction. This thermodynamic analysis is consistent with what is published in the literature: the decomposition of simple tertiary sulfonic esters is not catalyzed by the acids generated when they decompose.

Scheme 3.

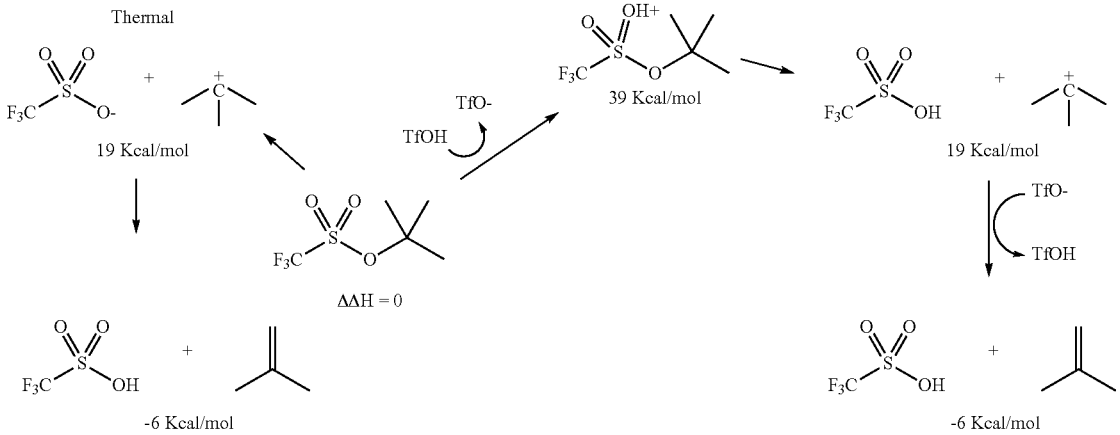

The sulfonic acid precursors provided or utilized in accordance with embodiments of the present invention can be thought of as acid amplifiers which have two parts, a "trigger" and a sulfonate group. The "trigger" is a leaving group which is bonded to the remainder of the molecule such that the bond is thermolytically stable at temperatures at which the substrates are processed, but in the presence of acid becomes sufficiently labile to enable elimination of the protonated leaving group and a proton, resulting in a carbon-carbon double bond. Two generic but non-limitative illustrations are provided in Scheme 4. As is illustrated in Scheme 4, in some embodiments of the invention, the leaving group is at the carbon labeled gamma and the sulfonate is at the carbon labeled alpha, i.e. there is hydrogen-bearing carbon atom between the carbon atoms to which the leaving group and sulfonate group are respectively attached.

Scheme 4

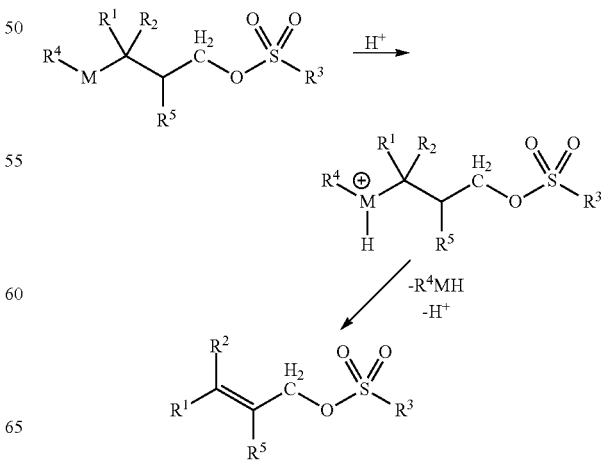

As shown illustratively in Scheme 4, as a result of elimination of the leaving group, the sulfonate becomes an allylic sulfonate, which, relative to the alkyl sulfonate that existed prior to elimination of the leaving group, is activated toward dissociation. Dissociation of the sulfonate moiety and loss of a proton results in a conjugated pi-system. This is non-limitatively illustrated in Scheme 5, in which $R^{1*}$, $R^{2*}$ and $R^{5*}$ denote $R^1$, $R^2$ and $R^5$, respectively, which have lost a proton.

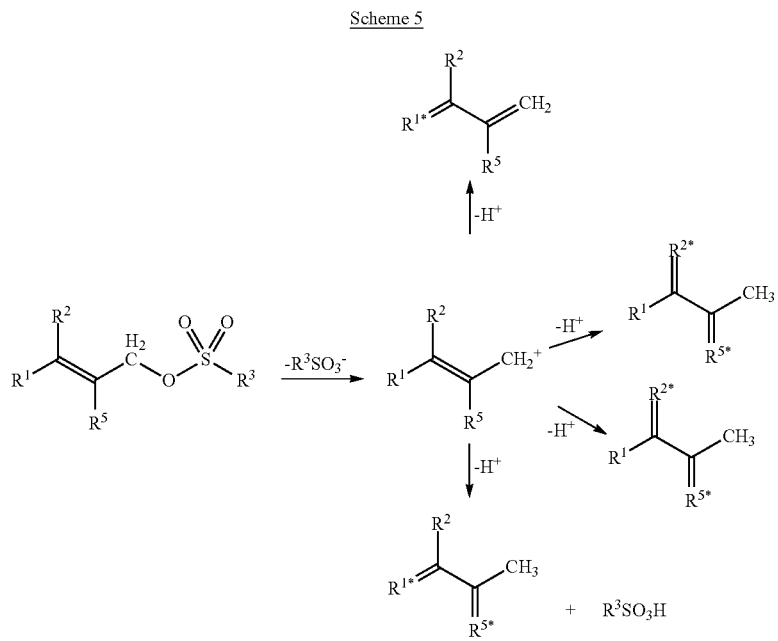

It will be appreciated that because the generation of the sulfonic acid by the sulfonic acid precursor is driven, in part, by the formation of a conjugated pi-system, molecules which will not enable the formation of such systems, e.g. molecules in which the sulfonate is adjacent to a bridgehead carbon such as 2- or 7-sulfonyl norbornane, are beyond the scope of embodiments of the present invention.

Photoresist polymers, i.e polymers suitable for use with photoacid generators and/or acid amplifiers in making photoresists are well-known in the art. See, e.g. U.S. Pat. No. 6,617,086, U.S. Pat. No. 6,803,169, US 2003/0134227 and US 2005/0147916, the contents of all of which are incorporated herein by reference. For example, by way of illustration, U.S. Pat. No. 6,803,169 describes various polymers, referred to therein as "deblocking resins", suitable for use in forming photoresists, in particular positive photoresists. Such polymers are referred to therein as containing "acid labile groups", i.e. moieties which can easily be removed by acid, "such as acid sensitive esters, carbonates, acetals, ketals and the like, which suitably may be pendant from a polymer backbone. Acid-labile groups that are integral to the polymer backbone also may be employed". Portions of the polymer in which acid labile groups have been removed by contact with photolytically generated acid will be susceptible to dissolution by base during the development of the photoresist. As explained therein, the deblocking resins may be deblocking resins as described in European Patent Published Application EP0813113A1 (corresponding to U.S. Pat. No. 5,861,231), European Patent Application 97115532 (corresponding to U.S. Pat. No. 5,861,231), U.S. Pat. No. 5,258,257, U.S. Pat. Nos. 4,968,581, 4,883,740, 4,810,613, 4,491,628 and 5,492,793. U.S. Pat. No. 6,803,169 goes on to state that:

"Preferred deblocking resins for use in the resists of the invention include polymers that contain both phenolic and non-phenolic units. For example, one preferred group of such polymers has acid labile groups substantially, essentially or completely only on non-phenolic units of the polymer. One preferred polymer binder has repeating units x and y of the following formula:

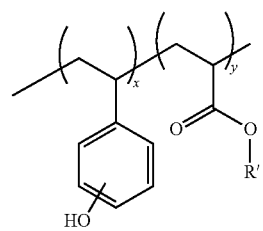

wherein the hydroxyl group be present at either the ortho, meta or para positions throughout the polymer, and $R^1$ is substituted or unsubstituted alkyl having 1 to about 18 carbon atoms, more typically 1 to about 6 to 8 carbon atoms. Tert-butyl is a generally employed $R^1$ group. An R' group may be optionally substituted by e.g. one or more halogen (particularly F, Cl or Br), $C_{1-8}$ alkoxy, $C_{2-8}$ alkenyl, etc. The depicted phenolic units of the polymer also may be optionally substituted by such groups. The units x and y may be regularly alternating in the polymer, or may be randomly interspersed through the polymer. Such copolymers can be readily formed. For example, for resins of the above formula, vinyl phenols and a substituted or unsubstituted alkyl acrylate such as t-butylacrylate and the like may be condensed under free radical conditions as known in the art. The substituted ester moiety, i.e. R'—O—C(=O)—, of the acrylate units serves as the acid labile groups of the resin and will undergo photoacid induced cleavage upon exposure of a coating layer of a photoresist containing the resin. The copolymer may have a Mw of from about 3,000 to about 50,000, for example about 10,000 to about 30,000 with a molecular weight distribution of about 3 or less; in some embodiments, a molecular weight distribution of about 2 or less. Such copolymers also may be prepared by such free radical polymerization or other known procedures and suitably will have a Mw of from about 3,000 to about 50,000, and a molecular weight distribution of about 3 or less, and in some embodiments about 2 or less.

"Additional preferred deblocking resins have acid labile groups on both phenolic and non-phenolic units of the polymer. One exemplary polymer binder has repeating units a, b and c of the following formula:

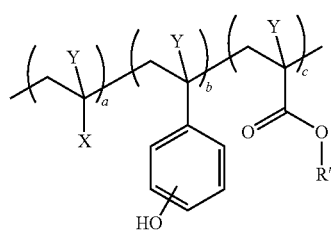

wherein R' group is a photoacid labile group as defined above for the other exemplary polymer; X is another repeat unit which may or may not contain a photoacid labile group; and each Y is independently hydrogen or $C_{1-6}$ alkyl, preferably hydrogen or methyl. The values a, b and c designate the molar amount of the polymer units. Those polymer units may be regularly alternating in the polymer, or may be randomly interspersed through the polymer. Suitable X groups may be aliphatic or aromatic groups such as phenyl, cyclohexyl, adamantyl, isobornylacrylate, methacrylate, isobornylmethacrylate, and the like. Such polymers may be formed in the same manner as described for the polymer above, and wherein the formed copolymer is reacted to provide the phenolic acid labile groups.

"Additional deblocking resins include at least three distinct repeating units of 1) units that contain acid-labile groups; 2) units that are free of reactive groups as well as hydroxy groups; and 3) aromatic or other units that contribute to aqueous developability of a photoresist containing the polymer as a resin binder. Particular examples of deblocking polymers of this type correspond to" the following formula:

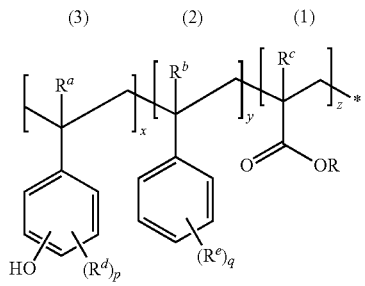

wherein R of units (1) is substituted or unsubstituted alkyl preferably having 1 to about 10 carbon atoms, more typically 1 to about 6 carbons. Branched alkyl, such as tert-butyl, are exemplary R groups. Also, the polymer may comprise a mixture of different R groups, e.g., by using a variety of acrylate monomers during the polymer synthesis.

$R^b$ groups of units (2) of the above formula each independently may be e.g. halogen (particularly F, Cl and Br), substituted or unsubstituted alkyl preferably having 1 to about 8 carbons, substituted or unsubstituted alkoxy preferably having 1 to about 8 carbon atoms, substituted or unsubstituted alkenyl preferably having 2 to about 8 carbon atoms, substituted or unsubstituted alkynyl preferably having 2 to about 8 carbons, substituted or unsubstituted alkylthio preferably having 1 to about 8 carbons, cyano, nitro, etc.; and q is an integer of from 0 (where the phenyl ring is fully hydrogen-substituted) to 5, for example 0, 1 or 2. Also, two $R^b$ groups on adjacent carbons may be taken together to form (with ring carbons to which they are attached) one, two or more fused aromatic or alicyclic rings having from 4 to about 8 ring members per ring. For example, two $R^b$ groups can be taken together to form (together with the depicted phenyl) a naphthyl or acenaphthyl ring. As with units (1), the polymer may comprise a mixture of different units (2) with differing $R^b$ groups or no $R^b$ groups (i.e. q=0) by using a variety of substituted or unsubstituted vinylphenyl monomers during the polymer synthesis.

$R^a$ groups of units (3) of the above Formula I each independently may be e.g. halogen (particularly F, Cl and Br), substituted or unsubstituted alkyl preferably having 1 to about 8 carbons, substituted or unsubstituted alkoxy preferably having 1 to about 8 carbon atoms, substituted or unsubstituted alkenyl preferably having 2 to about 8 carbon atoms, substituted or unsubstituted sulfonyl preferably having 1 to about to about 8 carbon atoms such as mesyl ($CH_3SO_2O$—), substituted or unsubstituted alkyl esters such as those represented by RCOO— where R is preferably an alkyl group preferably having 1 to about 10 carbon atoms, substituted or unsubstituted alkynyl preferably having 2 to about 8 carbons, substituted or unsubstituted alkylthio preferably having 1 to about 8 carbons, cyano, nitro, etc.; and p is an integer of from 0 (where the phenyl ring has a single hydroxy substituent) to 4, for example 0, 1 or 2. Also, two $R^a$ groups on adjacent carbons may be taken together to form (with ring carbons to which they are attached) one, two or more fused aromatic or alicyclic rings having from 4 to about 8 ring members per ring. For example, two $R^a$ groups can be taken together to form (together with the phenol depicted in Formula I) a naphthyl or acenaphthyl ring. As with units (1), the polymer may comprise a mixture of different units (3) with differing $R^a$ groups or no $R^a$ groups (i.e. p=0) by using a variety of substituted or unsubstituted vinylphenyl monomers during the polymer synthesis. As shown in Formula I above, the hydroxyl group of units (3) may be either at the ortho, meta or para positions throughout the copolymer. Para or meta substitution is generally preferred.

Each $R^a$, $R^b$ and $R^c$ substituent independently may be hydrogen or substituted or unsubstituted alkyl preferably having 1 to about 8 carbon atoms, more typically 1 to about 6 carbons, or more preferably 1 to about 3 carbons.

The above-mentioned substituted groups (i.e. substituted groups R and $R^a$ through $R^e$ of Formula I above) may be substituted at one or more available positions by one or more suitable groups such as halogen (particularly F, Cl or Br); $C_{1-8}$ alkyl; $C_{1-8}$ alkoxy; $C_{2-8}$ alkenyl; $C_{2-8}$ alkynyl; aryl such as phenyl; alkanoyl such as a $C_{1-6}$ alkanoyl of acyl and the like; etc. Typically a substituted moiety is substituted at one, two or three available positions.

In the above Formula I, x, y and z are the mole fractions or percents of units (3), (2) and (1) respectively in the copolymer. These mole fractions may suitably vary over rather wide values, e.g., x may be suitably from about 10 to 90 percent, more preferably about 20 to 90 percent; y may be suitably from about 1 to 75 percent, more preferably about 2 to 60 percent; and z may be 1 to 75 percent, more preferably about 2 to 60 percent.

Preferred copolymers of the above Formula I include those where the only polymer units correspond to the general structures of units (1), (2) and (3) above and the sum of the mole percents x, y and z equals one hundred. However, preferred polymers also may comprise additional units wherein the sum of x, y and z would be less than one hundred, although preferably those units (1), (2) and (3) would still constitute a major portion of the copolymer, e.g. where the sum of x, y and z would be at least about 50 percent (i.e. at least 50 molar percent of the polymer consists of units (1), (2) and (3)), more preferably the sum of x, y and z is at least 70 percent, and still more preferably the sum of x, y and z is at least 80 or 90 percent. See European Published Patent Application EP 0813113A1 [corresponding to U.S. Pat. No. 5,861,231] for detailed disclosure of free radical synthesis of copolymers of the above Formula I.

Additional resin binders include those that have acetalester and/or ketalester deblocking groups. Such resins are disclosed in EP 0829766A2 of the Shipley Company [corresponding to U.S. Pat. No. 6,090,526] and U. Kumar. For instance, suitable resins include terpolymers formed from hydroxystryene, styrene and acid labile components such as 1-propyloxy-1-ethylmethacrylate and the like.

Additional preferred polymers are disclosed in U.S. Pat. No. 6,136,501.

U.S. Pat. No. 6,803,169 states that "Polymers of the invention can be prepared by a variety of methods. One suitable method is free radical polymerization, e.g., by reaction of selected monomers to provide the various units as discussed above in the presence of a radical initiator under an inert atmosphere (e.g., $N_2$ or argon) and at elevated temperatures such as about 70° C. or greater, although reaction temperatures may vary depending on the reactivity of the particular reagents employed and the boiling point of the reaction solvent (if a solvent is employed). Suitable reaction solvents include e.g. tetrahydrofuran, dimethylformamide and the like. Suitable reaction temperatures for any particular system can be readily determined empirically by those skilled in the art based on the present disclosure. Monomers that can be reacted to provide a polymer of the invention can be readily identified by those skilled in the art based on the present disclosure. For example, suitable monomers include e.g. acrylate, including methacrylate, t-butylacrylate, acrylonitrile, methacrylonitrile, itaconic anhydride and the like. A variety of free radical initiators may be employed to prepare the copolymers of the invention. For example, azo compounds may be employed such as azo-bis-2,4-dimethylpentanenitrile. Peroxides, peresters, peracids and persulfates also could be employed.

"Unless indicated otherwise above, a polymer used as a resin binder component of a resist of the invention typically will have a weight average molecular weight ($M_w$) of 1,000 to about 100,000, more preferably about 2,000 to about 30,000, still more preferably from about 2,000 to 15,000 or 20,000, with a molecular weight distribution ($M_w/M_n$) of about 3 or less, more preferably a molecular weight distribution of about 2 or less. Molecular weights (either $M_w$ or $M_n$) of the polymers of the invention are suitably determined by gel permeation chromatography.

"Preferred polymers also will exhibit a sufficiently high $T_g$ to facilitate use of the polymer in a photoresist. Thus, preferably a polymer will have a $T_g$ greater than typical softbake (solvent removal) temperatures, e.g. a $T_g$ of greater than about 100° C., more preferably a $T_g$ of greater than about 110° C., still more preferably a $T_g$ of greater than about 120° C.

"For 193 nm imaging applications, preferably a resist resin binder component will be substantially free of any phenyl or other aromatic groups. For example, preferred polymers for use in 193 imaging contain less than about 1 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged 193 nm."

Photoresists also may contain other materials. For example, other optional additives include actinic and contrast dyes, anti-striation agents, plasticizers, speed enhancers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components. A common additive is a basic compound, such as tetrabutylammonium hydroxide (TBAH), tetrabutylammonium lactate, or tetrabutylammonium acetate, which can enhance resolution of a developed image. For resists imaged at 193 nm, an exemplary base is a hindered amine such as diazabicycloundecene, diazabicyclononene or diterbutylethanolamine. Such an amine may be suitably present in amount of about 0.03 to 5 to 10 weight percent, based on total solids (all components except solvent) of a resist composition.

The PAG blend component should be present in a photoresist formulation in amount sufficient to enable generation of a latent image in a coating layer of the resist. More specifically, the PAG blend will suitably be present in an amount of from about 0.5 to 40 weight percent of total solids of a resist, more typically from about 0.5 to 10 weight percent of total solids of a resist composition. The distinct PAGs of a blend suitably may be present in about equivalent molar amounts in a resist composition, or each PAG may be present in differing molar amounts. It is typically preferred however that each class or type of PAG is present in an amount of at least about 20 to 25 mole percent of total PAG present in a resist formulation.

The resin binder component of resists are typically used in an amount sufficient to render an exposed coating layer of the resist developable such as with an aqueous alkaline solution. More particularly, a resin binder will suitably comprise 50 to about 90 weight percent of total solids of the resist.

Photoresists are generally prepared following known procedures. For example, a resist can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether, propylene glycol monomethyl ether acetate; lactates such as ethyl lactate or methyl lactate, with ethyl lactate being preferred; proponiates, particularly methyl propionate, ethyl propionate and ethyl ethoxy propionate; a Cellosolve ester such as methyl Cellosolve acetate; an aromatic hydrocarbon such toluene or xylene; a ketone such as methylethyl ketone or cyclohexanone; and the like. Typically the solids content of the photoresist varies between 5 and 35 percent by weight of the total weight of the photoresist composition.

The photoresists can be used in accordance with known procedures. Though photoresists may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image.

The substrate suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also employed, e.g. glass substrates, indium tin oxide coated substrates and the like. As discussed above, it has been found that highly resolved resist relief images can be formed on substrates that can be difficult to pattern fine images, such as boron phosphorus silicate glass. A liquid coating resist composition may be applied by any standard means such as spinning, dipping or roller coating.

Rather than applying a resist composition directly onto a substrate surface, a coating layer of an antireflective coating composition may be first applied onto a substrate surface and the photoresist coating layer applied over the underlying antireflective coating. A number of antireflective coating compositions may be employed including the compositions disclosed in European Applications Publication Nos. 0542008A1 and 0813114A2, both of the Shipley Company. For resists to be imaged at 248 nm, an antireflective composition that contains a resin binder with anthracene units preferably may be employed.

The exposure energy should be sufficient to effectively activate the photoactive component of the radiation sensitive system to produce a patterned image in the resist coating layer. Suitable exposure energies typically range from about 10 to 300 mJ/cm². An exposure wavelength in the deep U.V. range often will be used for the photoresists of the invention, particularly exposure wavelengths of sub-250 nm or sub-200 nm such as about 248 nm or 193 nm. The exposed resist coating layer can be thermally treated after exposure and prior to development, with suitable post-exposure bake temperatures being from about e.g. 50° C. or greater, more specifically from about 50 to 160° C. After development, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

Thus, in embodiments of the present invention, photoresist polymers known in the art, such as those described in U.S. Pat. No. 6,803,169 or in the references cited therein and which are mentioned in the quoted text above may be used. Resists per se in accordance with embodiments of the present invention may be likewise be prepared in accordance with methods known in the art, for example as described in U.S. Pat. No. 6,803,169, e.g. by dissolving the components of the photoresist in a suitable solvent such as, e.g., a glycol ether such as 2-methoxyethyl ether (diglyme), ethylene glycol monomethyl ether, propylene glycol monomethyl ether, propylene glycol monomethyl ether acetate; lactates such as ethyl lactate or methyl lactate; proponiates, particularly methyl propionate, ethyl propionate and ethyl ethoxy propionate; a Cellosolve ester such as methyl Cellosolve acetate; an aromatic hydrocarbon such toluene or xylene; a ketone such as methylethyl ketone or cyclohexanone; and the like; and applying the solution to a substrate and baking Typically the solids content of the photoresist varies between 5 and 35 percent by weight of the total weight of the photoresist composition.

In some embodiments, the sulfonic acid precursor may be included in the photoresist composition as a molecule separate from the polymer. In other embodiments, the sulfonic acid precursor may be incorporated into the polymer chain. For example, if the photoresist polymer is a terpolymer having the structure

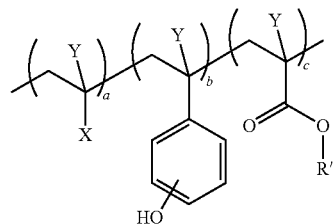

as defined in U.S. Pat. No. 6,803,169, $R^1$ may be the sulfonic acid precursor. This can be accomplished, for example, by including in the mix of monomers used to produce the polymer an amount of a compound of formula:

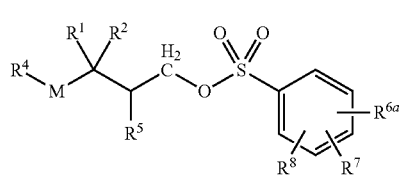

I wherein $R^{6a}$ is chosen from —$CH_2Br$, —$CH$=$CH_2$, and —$OCH_2CH_2Br$, thus allowing the compound to be incorporated into a polymer backbone. If another acrylic acid-derived monomer containing a different group R', e.g. tert-butyl, is also employed in the polymer synthesis, this will result in a quadpolymer rather than the terpolymer shown. Alternatively, a small amount of the quadpolymer (or terpolymer) incorporating the sulfonic acid generating compound (only) may be synthesized, and in preparing the photoresist this quad- or terpolymer may be blended with a larger amount of a terpolymer in which $R^1$ is not a sulfonic acid generating group.

The amount of sulfonic acid precursor employed may be up to 40 mol. % of the solids of the photoresist composition, for example, between 1 and 30 mol. % of the solids of the photoresist composition, for example 2 to 20 mol. %. In the case where the sulfonic acid precursor is incorporated into the polymer, the monomer may constitute up to 40 mol. % of the polymer, for example 1 to 30% mol. % or 2 to 20% mol. %.

In some embodiments of the present invention, the photoresist composition includes a photoacid generator (PAG). PAGs are well-known in the art, see for example EP 0164248, EP 0232972, EP 717319A1, U.S. Pat. No. 4,442,197, U.S. Pat. No. 4,603,101, U.S. Pat. No. 4,624,912, U.S. Pat. No. 5,558,976, U.S. Pat. No. 5,879,856, U.S. Pat. No. 6,300,035, U.S. Pat. No. 6,803,169 and US 2003/0134227, the contents of all of which are incorporated herein by reference, and include, for example, di-(t-butylphenyl)iodonium triflate, di-(t-butylphenyl)iodonium perfluorobutanesulfonate, di-(4-tert-butylphenyl)iodonium perfluoroctanesulfonate, di-(4-t-butylphenyl)iodonium o-trifluoromethylbenzenesulfonate, di-(4-t-butylphenyl)iodonium camphorsulfonate, di-(t-butylphenyl)iodonium perfluorobenzenesulfonate, di-(t-butylphenyl)iodonium p-toluenesulfonate, triphenyl sulfonium triflate, triphenyl sulfonium perfluorobutanesulfonate, triphenyl sulfonium perfluoroctanesulfonate, triphenyl sulfonium o-trifluoromethylbenzenesulfonate, triphenyl sulfonium camphorsulfonate, triphenyl sulfonium perfluorobenzenesulfonate, triphenyl sulfonium p-toluenesulfonate, N-[(trifluoromethane sulfonyl)oxy]-5-norbornene-2,3-dicarboximide, N-[(perfluorobutane sulfonyl)oxy]-5-norbornene-2,3-dicarboximide, N-[(perfluorooctane sulfonyl)oxy]-5-norbornene-2,3-dicarboximide, N-[(o-trifluoromethylbenzene sulfonyl)oxy]-5-norbornene-2,3-dicarboximide, N-[(camphor sulfonyl)oxy]-5-norbornene-2,3-dicarboximide, N-[(perfluorobenzene sulfonyl)oxy]-5-norbornene-2,3-dicarboximide, N-[(p-toluenesulfonate sulfonyl)oxy]-5-norbornene-2,3-dicarboximide, phthalimide triflate, phthalimide perfluorobutanesulfonate, phthalimide perfluoroctanesulfonate, phthalimide o-trifluoromethylbenzenesulfonate, phthalimide camphorsulfonate, phthalimide perfluorobenzenesulfonate, phthalimide p-toluenesulfonate, diphenyl-iodonium triflate, diphenyl-iodonium perfluorobutanesulfonate, diphenyl-iodonium perfluoroctanesulfonate., diphenyl-iodonium o-trifluoromethylbenzenesulfonate, diphenyl-iodonium camphorsulfonate, diphenyl-iodonium perfluorobenzenesulfonate, diphenyl-iodonium p-toluenesulfonate. U.S. Pat. No. 6,803,169 describes the use combinations of a variety of PAGs.

In some embodiments of the invention, the PAG is active at a wavelength of about 193 nm or shorter. In some embodiments, the PAG is active at a wavelength of about 193 nm. In some embodiments, the PAG is active at a wavelength of about 13.5 nm.

Although the acid generated by the PAG need not be the same as the sulfonic acid generated by the sulfonic acid precursor, in some embodiments the PAG and sulfonic acid precursor generate the same acid. It will also be appreciated that in some embodiments, the sulfonic acid precursor itself can act as a PAG. In general in such cases, the sulfonic precursor will be a less efficient PAG, i.e. generate less acid per number of photons, electrons or ions, in accordance with the type of radiation used, than PAGs which are known in the art and generate the same acid. It will also be appreciated that although it will generally be necessary to heat the sulfonic acid precursor in the presence of a small amount of acid to generate sulfonic acid, in some embodiments the sulfonic acid precursor will be active in the presence of acid at a temperature of 18 to 30 degrees Celsius.

Syntheses

In general, compounds per se or for use in accordance with embodiments of present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

EXAMPLES

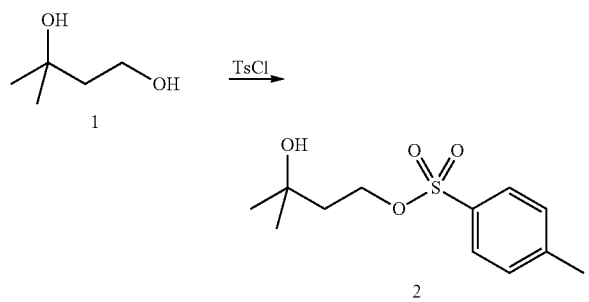

3-Hydroxy-3-methylbutyl 4-methylbenzenesulfonate (2)

A mixture of 3-methyl-1,3-methanebutane diol (2.00 g, 19.2 mmol), tosyl chloride (5.491 g, 28.8 mmol) in dry pyridine (20 mL) was stirred at 0° C. for 2 hours, poured into the cold HCl (50 mL, 2 N), and extracted with ethyl acetate. The organic phase was washed with HCl (4×50 mL, 2 N), brine (1×25 mL), dried over MgSO$_4$, and evaporated to dryness. (3.72 g, 97%). $^1$H NMR (CDCl$_3$): δ 1.17 (6H, s), 1.82 (2H, t, J=6.8 Hz), 2.41 (3H, s), 4.17 (2H, t, J=6.8 Hz), 7.31, 7.75 (each 2H, d, J=8.2 Hz).

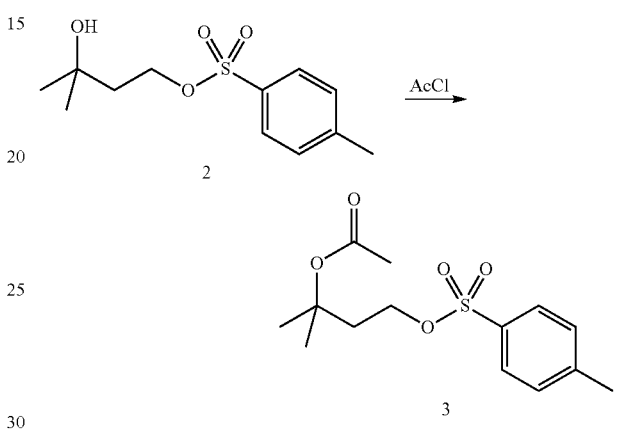

2-Methyl-4-(tosyloxy)butan-2-yl acetate (3)

To a mixture of the alcohol 2 (0.500 g, 1.937 mmol), ZrOCl$_2$.8.H$_2$O (0.0031 g, 0.5 mol %) in methylene chloride (5 mL), acetyl chloride (0.304 g, 3.87 mmol) is added and the reaction is stirred for overnight at 20° C. The reaction on completion, is diluted with methylene chloride (5 mL) and washed with saturated sodium bicarbonate (2×10 mL), brine (1×10 mL) and dried. The solvent is evaporated to get the crude product. $^1$H NMR (400 MHz, CDCl$_3$): δ 1.54 (s, 6H), 1.59 (s, 3H), 2.14-2.07 (m, 2H), 2.43 (s, 3H), 4.26 (dt, J=6.9, 13.5, 3H), 7.33 (d, J=7.9, 2H), 7.77 (d, J=8.2, 2H).

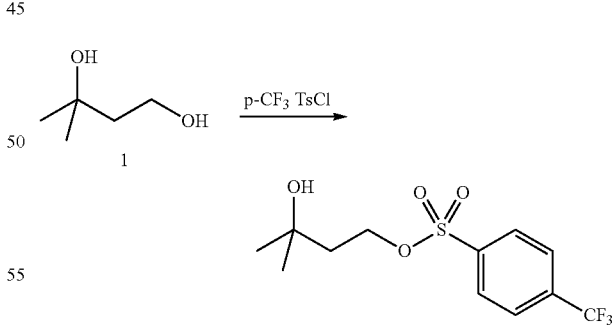

3-Hydroxy-3-methylbutyl 4-(trifluoromethyl)benzenesulfonate (4)

A mixture of 3-methyl-1,3-methanebutane diol (2.00 g, 19.2 mmol), (4-trifluoromethyl)benzene sulfonyl chloride (7.046 g, 28.8 mmol) in dry pyridine (20 mL) was stirred at 0° C. for 2 hours, poured into the cold HCl (50 mL, 2 N), and extracted with ethyl acetate. The organic phase was washed with HCl (4×50 mL, 2 N), brine (1×25 mL), dried over MgSO$_4$, and evaporated to dryness. (3.72 g, 97%). $^1$H NMR (400 MHz, CDCl$_3$): δ 1.21 (s, 6H), 1.87 (t, J=6.9, 2H), 2.03 (d, J=14.0, 2H), 4.26 (t, J=6.9, 2H), 7.81 (d, J=8.6, 2H), 8.03 (d, J=8.1, 2H). Repeat synthesis: To a solution of 3-methyl-1,3-butane diol (1.9 g, 18.2 mmol) in pyridine (15 mL) was added p-(trifluoromethyl)benzenesulfonyl chloride (3.67 g, 15 mmol). The solution was stirred at 0° C. for 2 h. The reaction mixture was diluted with ethyl acetate (40 mL) and washed with 1 M HCl (3×50 mL), saturated aqueous NaHCO3 (1×50 mL) and saturated aqueous NaCl (1×50 mL). The organics were dried over Na2SO4 and concentrated to give a white low melting point solid (3.33 g, 71%). $^1$H NMR (400 MHz CDCl$_3$) δ 8.04 (d, 2H, J=8.0 Hz), 7.81 (d, 2H, J=8.0 Hz), 4.72 (t, 2H, J=7.0 Hz), 1.87 (t, 2H, J=7.0 Hz), 1.21 (s, 6H). Anal. Calcd. For C$_{12}$H$_{15}$F$_3$O$_4$S: C, 46.15; H, 4.84. Found: C, 46.14; H, 4.90.

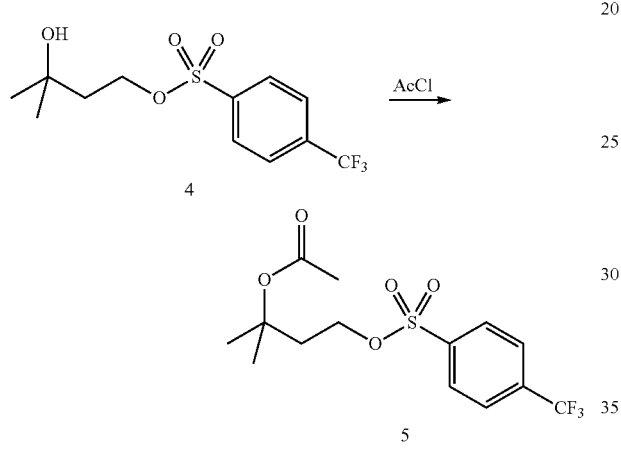

2-Methyl-4-(4-(trifluoromethyl)phenylsulfonyloxy) butan-2-yl acetate (5)

To a mixture of the alcohol 4 (0.500 g, 1.6 mmol), ZrOCl$_2$.8.H$_2$O (0.0025 g, 0.5 mol %) in methylene chloride (5 mL), acetyl chloride (0.251 g, 3.2 mmol) is added and the reaction is stirred for overnight at 20° C. The reaction on completion, is diluted with methylene chloride (5 mL) and washed with saturated sodium bicarbonate (2×10 mL), brine (1×10 mL) and dried. The solvent is evaporated to get the crude product. $^1$H NMR (400 MHz, CDCl$_3$) δ1.56 (d, J=8.0, 6H), 1.60 (d, J=8.0, 5H), 2.14 (t, J=6.8, 2H), 4.33 (t, J=6.8, 2H), 7.82 (d, J=8.1, 2H), 8.04 (d, J=8.0, 2H).

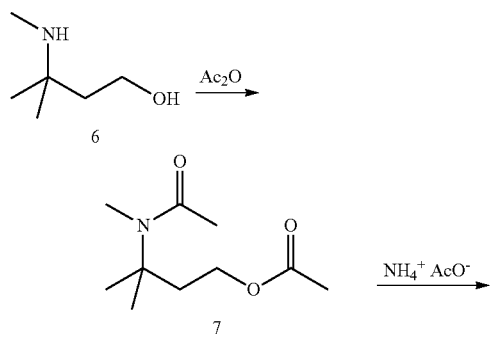

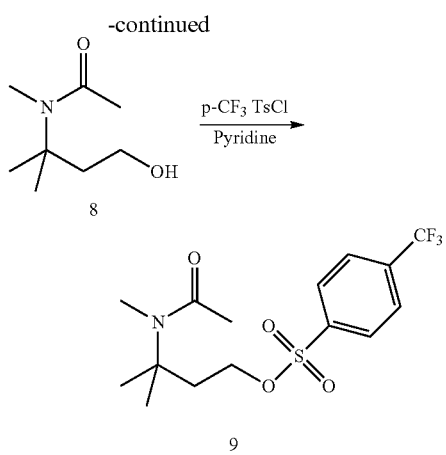

3-methyl-3-(N-methylacetamido)butyl 4-(trifluoromethyl)benzene-sulfonate (4)

3-Methyl-3-methylamino-1-butanol[1](6) is reacted with acetic anhydride (3 eq.) in methylene chloride at 20° C. followed by aqueous work-up to yield 3-methyl-3-(N-methylacetamido)butyl acetate (7). The primary acetate is removed by reacting (7) with ammonium acetate (2 eq.) in isopropanol yielding N-(4-hydroxy-2-methylbutan-2-yl)-N-methylacetamide (8). The primary alcohol (8), is reacted with (4-trifluoromethyl)benzene sulfonyl chloride in dry pyridine at 0° C. for 2 hours, followed by aqueous work-up yielding 3-methyl-3-(N-methylacetamido)butyl 4-(trifluoromethyl)-benzenesulfonate (9).

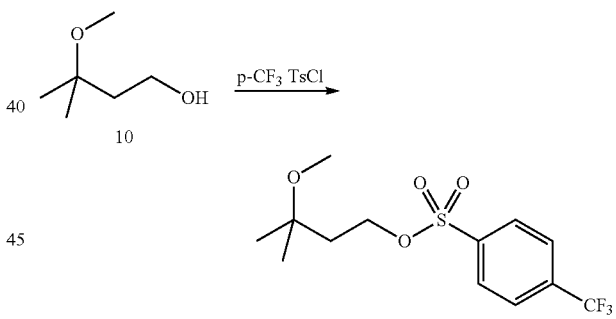

3-methoxy-3-methylbutyl 4-(trifluoromethyl)benzenesulfonate (11)

To a solution of 3-methoxy-3-methylbutane-1-ol (10) (0.58 g, 4.9 mmol) in pyridine (5 mL) was added p-(trifluoromethyl)benzenesulfonyl chloride (0.98 g, 4 mmol). The solution was stirred at rt for 3.5 h. The reaction mixture was diluted with ethyl acetate (25 mL) and washed with 1 M HCl (6×25 mL), saturated aqueous NaHCO$_3$ (1×25 mL) and saturated aqueous NaCl (1×25 mL). The organics were dried over Na$_2$SO$_4$ and concentrated to give an oil (0.53 g, 40%). $^1$H NMR (400 MHz CDCl$_3$) δ 8.03 (d, 2H, J=8.0 Hz), 7.81 (d, 2H, J=8.0 Hz), 4.19 (t, 2H, J=7.3 Hz), 3.09 (s, 3H), 1.88 (t, 2H, J=7.3 Hz), 1.12 (s, 6H); $^{19}$F NMR (400 MHz CDCl$_3$) δ −66.45 (s). Anal. Calcd. For C$_{13}$H$_{17}$F$_3$O$_4$S: C, 47.85; H, 5.25. Found: C, 47.72; H, 5.05. (11).

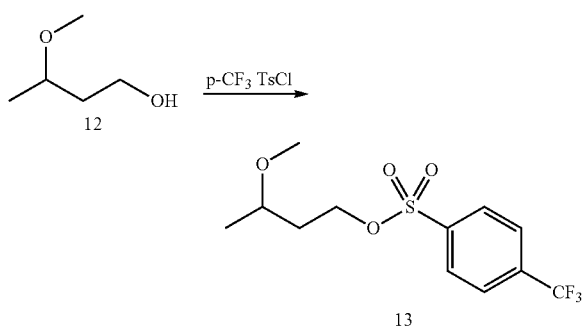

3-methoxybutyl 4-(trifluoromethyl)benzenesulfonate (13)

To a solution of 3-methoxybutane-1-ol (12) (0.58 g, 4.9 mmol) in pyridine (5 mL) was added p-(trifluoromethyl)-benzenesulfonyl chloride (0.98 g, 4 mmol). The solution was stirred at rt for 3.5 h. The reaction mixture was diluted with ethyl acetate (25 mL) and washed with 1 M HCl (6×25 mL), saturated aqueous NaHCO$_3$ (1×25 mL) and saturated aqueous NaCl (1×25 mL). The organics were dried over Na$_2$SO$_4$ and concentrated to give an oil (13) (0.53 g, 40%). $^1$H NMR (400 MHz CDCl$_3$) δ 8.03 (d, 2H, J=8.1 Hz), 7.81 (d, 2H, J=8.3 Hz), 4.19 (m, 2H), 3.35 (m, 1H), 3.18 (s, 3H), 1.78 (m, 2H), 1.09 (d, 3H, J=6.0 Hz); $^{19}$F δ (s). Anal. Calcd. For C$_{12}$H$_{15}$F$_3$O$_4$S: C, 46.15; H, 4.84. Found: C, 45.99; H, 4.64.

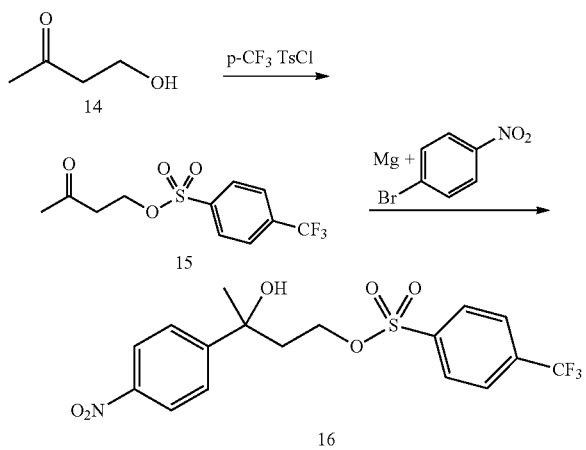

3-hydroxy-3-(4-nitrophenyl)butyl 4-(trifluoromethyl)benzenesulfonate (16)

4-Hydroxybutane-2-one (14) is reacted with (4-trifluoromethyl)benzene sulfonyl chloride (0.9 eq.) in dry pyridine at 20° C. for 2 hours, followed by aqueous work-up to yield 3-oxobutyl 4-(trifluoromethyl)benzenesulfonate (15). Magnesium turnings are weighed into a dry flask and dissolved in dry tetrahydrofuran. 1-Bromo-4-nitrobenzene (1 eq.) is added to the solution to give the Grignard reagent, (4-nitrophenyl)magnesium bromide. The sulfonate ester dissolved in diethyl ether or THF is added drop-wise to the Grignard reagent at 0° C. and reacted for 30 minutes. The reaction is quenched with ice and the solution is acidified with HCl. Extraction with diethyl ether yields the product 3-hydroxy-3-(4-nitrophenyl)butyl 4-(trifluoromethyl)benzenesulfonate (16).

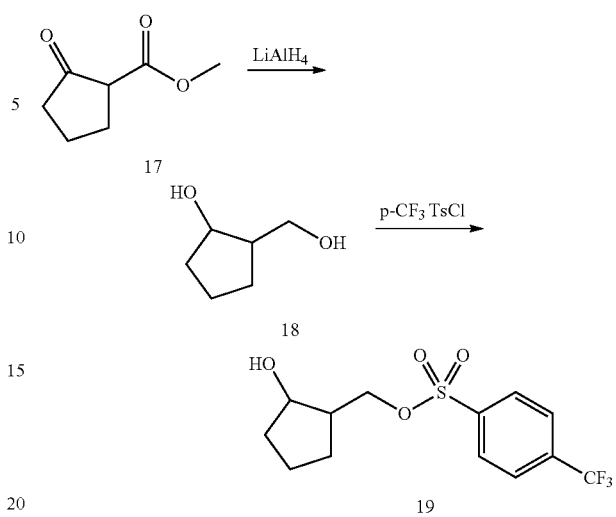

(2-hydroxycyclopentyl)methyl 4-(trifluoromethyl)benzenesulfonate (19)

Methyl 2-oxocyclopentanecarboxylate (17) is reacted with lithium aluminum hydride (5 eq.) in tetrahydrofuran at 0° C. for 4 hours. The reaction is then quenched with ice and acidified with HCl. The Solution is then washed with diethyl ether, and the aqueous phase is then continuously extracted over night to yield the product 2-(hydroxymethyl)cyclopentanol (18). A solution of 2-(hydroxymethyl)cyclopentanol (1.5 eq.) is then reacted with 4-(trifluoromethyl)benzene-1-sulfonyl chloride (1 eq.) and triethylamine (1 eq.) in dichloromethane at 0° C. for 2 hours. Aqueous workup yields the product, (2-hydroxycyclopentyl)methyl 4-(trifluoromethyl)benzenesulfonate(19).

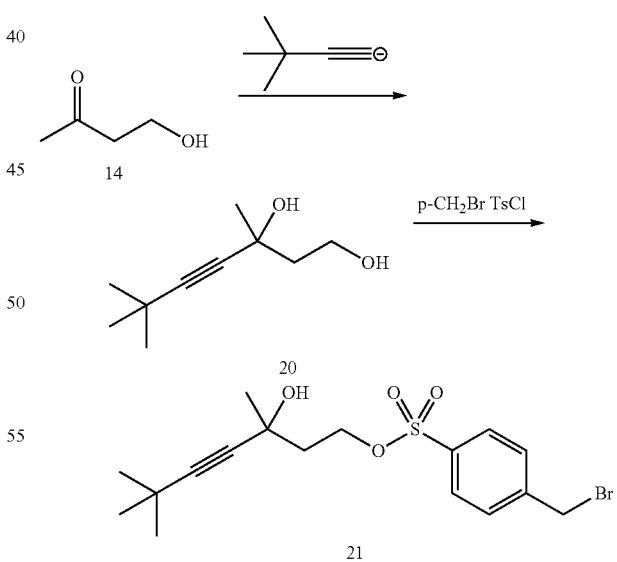

3-hydroxy-3,6,6-trimethylhept-4-ynyl 4-(bromomethyl)benzenesulfonate (21)

3,3-Dimethylbut-1-yne (3.0 eq.) in dry tetrahydrofuran is reacted with n-butyllithium (2.5 eq.) at −78° C. The solution is stirred for 30 minutes, when 4-hydroxybutan-2-one (14) is added and the solution is stirred for 6 hours. The solution is quenched with ice chips followed by HCl and extracted with diethylether to yield the product 3,6,6-trimethylhept-4-yne-1,3-diol(20). A solution of 3,6,6-trimethylhept-4-yne-1,3-diol (1.5 eq.) is then reacted with 4-(bromomethyl)benzene-1-sulfonyl chloride (1 eq.) and triethylamine (1 eq.) in dichloromethane at 0° C. for 2 hours. Aqueous workup yields the product, 3-hydroxy-3,6,6-trimethylhept-4-ynyl 4-(bromomethyl)benzenesulfonate(21).

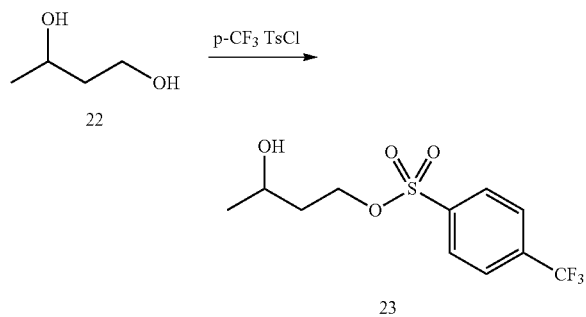

3-Hydroxybutyl 4-(trifluoromethyl)benzenesulfonate (23)

A solution of 1,3-butanediol (2.00 g, 22.193 mmol) and triethylamine (2.695 g, 26.631 mmol) in 10 mL of methylene chloride was stirred at −20° C. under nitrogen. (4-trifluoromethyl)benzene sulfonyl chloride (5.429 g, 22.193 mmol) in 10 mL of methylene chloride was added drop wise to the solution, over 1 hr. The reaction was kept at −20° C. for an additional 3 hours and then stirred at room temperature for 24 hours. The reaction was quenched with water and then washed with 10% aqueous HCl (5×30 mL), sat. NaHCO$_3$ (3×20 mL), H$_2$O (2×20 mL) and brine (1×20 mL). The organic layer was dried over Na$_2$SO$_4$ and the solvent was evaporated under reduced pressure. The product obtained was purified by column chromatography to get a white solid. (1.541 g, 23% yield). $^1$H NMR (400 MHz, CDCl$_3$) δ1.19 (d, J=6.29, 3H, CH$_3$), 1.66-1.76 (m, 1H, CH$_2$), 1.80-1.91 (m, 1H, CH$_2$), 3.93 (br. s, 1H, CH—OH), 4.14-4.23 (m, 1H, CH$_2$O—SO$_2$), 4.25-4.36 (m, 1H, CH$_2$O—SO$_2$), 7.81 (d, J=8.08, 2H, aromatic), 8.04 (d, J=8.71, 2H, aromatic). Repeat synthesis: To a solution of 1,3-butane diol (4.34 g, 48 mmol) and TEA (3.19 g, 31.5 mmol) in CH$_2$Cl$_2$ (20 mL) at 0° C. was added p-(trifluoromethyl)benzene-sulfonyl chloride (3.97 g, 16.2 mmol) dissolved in CH$_2$Cl$_2$ (20 mL). The solution was stirred at 0° C. for 2 h. Saturated aqueous NaHCO$_3$ (15 mL) was added to the solution and mixture was stirred at rt for 40 min. The organics were extracted with CH$_2$Cl$_2$ (50 mL) and washed with 1 M HCl (3×25 mL) and saturated aqueous NaCl (1×25 mL). The organics were dried over Na$_2$SO$_4$ and concentrated to give the desired product (3.28 g, 65%). $^1$H NMR (400 MHz CDCl$_3$) δ 8.02 (d, 2H, J=8.2 Hz), 7.80 (d, 2H, J=8.3), 4.29 (m, 1H), 4.17 (m, 1H), 3.91 (m, 1H), 1.83 (m, 1H), 1.70 (m, 1H), 1.17 (d, 3H, J=6.2 Hz); Anal. Calcd. For C$_{11}$H$_{13}$F$_3$O$_4$S: C, 44.29; H, 4.39. Found: C, 44.16; H, 4.17.

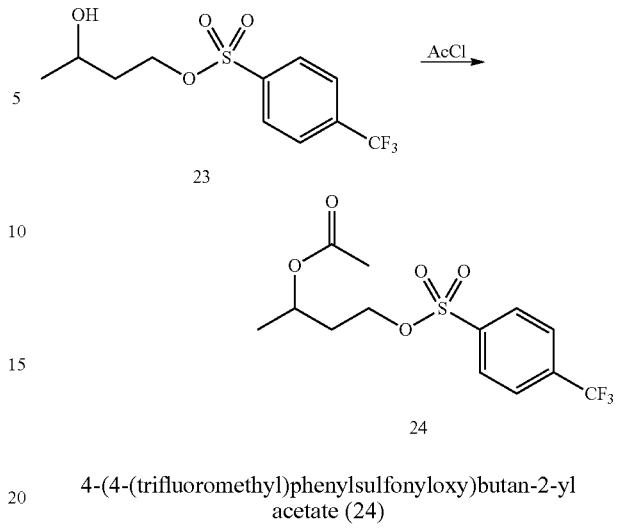

4-(4-(trifluoromethyl)phenylsulfonyloxy)butan-2-yl acetate (24)

3-Hydroxybutyl 4-(trifluoromethyl)benzenesulfonate (23) is reacted with acetyl chloride (1.5 eq.) in the presence of ZrOCl$_2$38H$_2$0 in methylene chloride and is left to stir over night. An aqueous workup yields the product, 4-(4-(trifluoromethyl)phenylsulfonyloxy)butan-2-yl acetate(24).

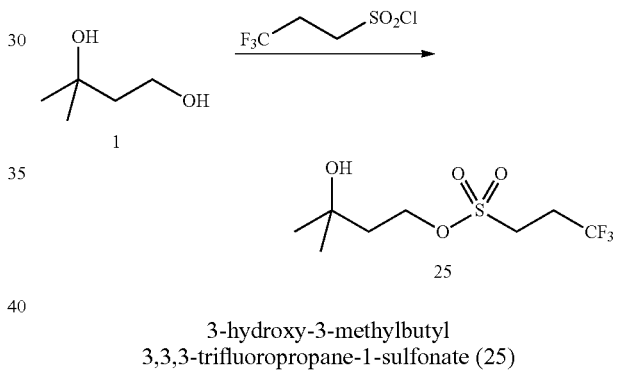

3-hydroxy-3-methylbutyl 3,3,3-trifluoropropane-1-sulfonate (25)

3-Methylbutane-1,3-diol (1) is reacted with 3,3,3-trifluoropropane-1-sulfonyl chloride (0.66 eq.) and triethylamine (0.66 eq.) in dichloromethane at 0° C. for 2 hours. Aqueous workup yields the product, 3-hydroxy-3-methylbutyl 3,3,3-trifluoropropane-1-sulfonate(25).

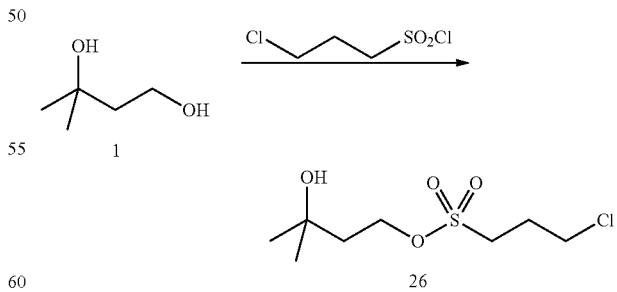

3-hydroxy-3-methylbutyl 3-chloropropane-1-sulfonate (26)

3-Methylbutane-1,3-diol (1) is reacted with 3-chloropropane-1-sulfonyl chloride (0.66 eq.) and triethylamine (0.66 eq.) in dichloromethane at 0° C. for 2 hours. Aqueous workup yields the product, 3-hydroxy-3-methylbutyl 3-chloropropane-1-sulfonate(26).

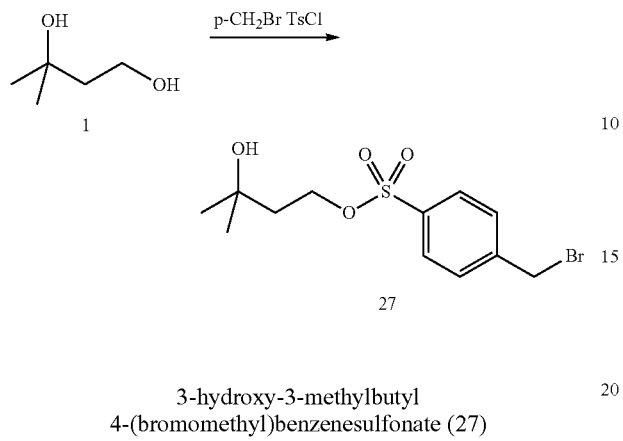

3-hydroxy-3-methylbutyl 4-(bromomethyl)benzenesulfonate (27)

3-Methyl-1,3-methanebutane diol (2.00 g, 19.2 mmol) and (4-bromomethyl)benzene sulfonyl chloride (5.491 g, 28.8 mmol) in dry pyridine (20 mL) was stirred at 0° C. for 2 hours, quenched with cold HCl (50 mL, 2 N), and extracted with ethyl acetate. The organic phase was washed with additional HCl (4×50 mL, 2 N), brine (1×25 mL), dried over MgSO$_4$, and evaporated to dryness to get a colorless oil. (1.214 g, 19%). $^1$H NMR (CDCl$_3$): δ 1.21 (s, 6H, CH$_3$), 1.86 (t, J=6.8 Hz, 2H, CH$_2$), 4.23 (t, J=6.81, 2H, CH$_2$—OSO$_2$), 4.61 (s, 2H, CH$_2$-arom.), 7.56 (d, J=8.4 Hz, 2H, arom.) 7.89 (d, J=8.8 Hz, 2H, arom.).

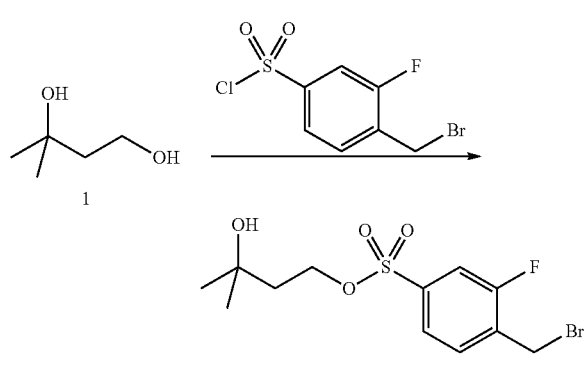

3-hydroxy-3-methylbutyl 4-(bromomethyl)-3-fluorobenzenesulfonate(28)

4-(Bromomethyl)-3-fluorobenzenesulfonyl chloride[2] is reacted with 3-methylbutane-1,3-diol(1) in anhydrous pyridine at 0° C. for 2 hours, followed by aqueous work-up to yield 3-hydroxy-3-methylbutyl 4-(bromomethyl)-3-fluorobenzenesulfonate (28).

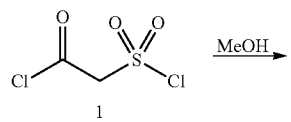

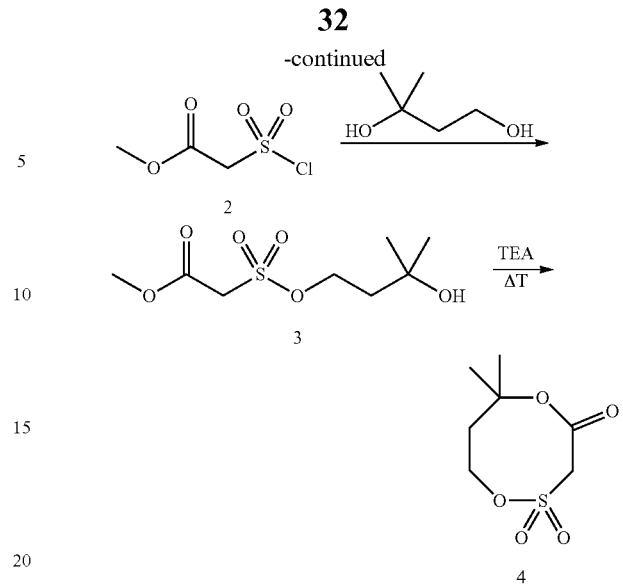

Cyclic Acetosulphonic Acid Amplifier(4)

2-(Chlorosulfonyl)acetyl chloride(1) is reacted with 1 equivalent of methanol, at cold temperatures, to produce methyl 2-(chlorosulfonyl)acetate(2). In the same pot, 3-methyl-1,3-butanediol is added and the reaction is worked up in the conventional manner to produce methyl 2-(3-hydroxy-3-methylbutoxysulfonyl)acetate(3). Compound 3 is then heated in triethylamine while methanol is distilled off to produce the cyclic acid amplifier (4).

3-Hydroxy-3-methylbutyl 2-(trifluoromethyl)benzenesulfonate

To a solution of 3-methyl-1,3-butane diol (2.5 g, 21 mmol) and TEA (1.63 g, 16 mmol) in CH$_2$Cl$_2$ (15 mL) was added o-(trifluoromethyl)benzenesulfonyl chloride (2.03 g, 8.3 mmol) dissolved in CH$_2$Cl$_2$ (20 mL). The solution was stirred at rt for 7 h. The reaction mixture was diluted with CH$_2$Cl$_2$ (75 mL) and washed with 1 M HCl (2×25 mL), saturated aqueous NaHCO$_3$ (1×25 mL) and saturated aqueous NaCl (1×25 mL). The organics were dried over Na$_2$SO$_4$ and concentrated to give a crude mixture. Silica gel chromatography with ethyl acetate in hexanes yielded the desired product (1.73 g, 66%). $^1$H NMR (400 MHz CDCl$_3$) δ 8.23 (m, 1H), 7.91 (m, 1H), 7.75 (m, 2H), 4.32 (t, 2H, J=7.0 Hz), 1.91 (t, 2H, J=7.0 Hz) 1.22 (s, 6H). Anal. Calcd. For C$_{12}$H$_{15}$F$_3$O$_4$S: C, 46.15; H, 4.84. Found: C, 45.73; H, 4.88.

3-Hydroxy-3-methylbutyl 2,3,4,5,6-pentafluorobenzenesulfonate

To a solution of 3-methyl-1,3-butane diol (0.79 g, 7.5 mmol) and TEA (0.37 g, 3.6 mmol) in CH$_2$Cl$_2$ (7 mL) at) 0° C. was added pentafluorobenzenesulfonyl chloride (0.80 g, 3.0 mmol). The solution was stirred at 0° C. for 1.5 h. Saturated aqueous NaHCO$_3$ (10 mL) was added to the solution and the mixture was stirred at rt for 15 min. The organics were extracted with CH$_2$Cl$_2$ and washed with 0.5 M HCl (1×20 mL) and saturated aqueous NaCl (1×20 mL). The organics were dried over Na$_2$SO$_4$ and concentrated to give a crude mixture. Silica gel chromatography with (30% ethyl acetate in hexanes) yielded the desired product as a white crystalline low melting point solid (0.69 g, 66%). $^1$H NMR (400 MHz CDCl$_3$) δ 4.49 (t, 2H, J=7.0 Hz), 1.97 (t, 2H, J=7.0 Hz) 1.27 (s, 6H). Anal. Calcd. For C$_{11}$H$_{11}$F$_5$O$_4$S: C, 39.53; H, 3.32. Found: C, 39.54; H, 3.22.

3-Methoxy-3-methylbutyl 2-(trifluoromethyl)benzenesulfonate

To a solution of 3-methoxy-3-methylbutane-1-ol (2.8 g, 24 mmol) and TEA (1.6 g, 16 mmol) in CH$_2$Cl$_2$ (15 mL) was added o-(trifluoromethyl)benzenesulfonyl chloride (1.9 g, 8 mmol) dissolved in CH$_2$Cl$_2$ (20 mL). The solution was stirred at rt for 4 h. Saturated aqueous NaHCO$_3$ (15 mL) was added to the solution and mixture was stirred at rt for 30 min. The organics were extracted with CH$_2$Cl$_2$ (75 mL) and washed with 1 M HCl (2×25 mL), saturated aqueous NaHCO$_3$ (1×25 mL) and saturated aqueous NaCl (1×25 mL). The organics were dried over Na$_2$SO$_4$ and concentrated to give a crude mixture. Silica gel chromatography with ethyl acetate in hexanes yielded the desired product (2.1 g, 81%). $^1$H NMR (400 MHz CDCl$_3$) δ 8.23 (m, 1H), 7.91 (m, 1H), 7.74 (m, 2H), 4.25 (t, 2H, J=7.5 Hz), 3.10 (s, 1H), 1.92 (t, 2H, J=7.5 Hz) 1.13 (s, 6H). Anal. Calcd. For C$_{13}$H$_{17}$F$_3$O$_4$S: C, 47.85; H, 5.25. Found: C, 47.95; H, 5.11.

3-Methoxy-3-methylbutyl 2,3,4,5,6-pentafluorobenzenesulfonate

To a solution of 3-methoxy-3-methylbutane-1-ol (1.07 g, 9 mmol) and TEA (0.61 g, 6 mmol) in CH$_2$Cl$_2$ (12 mL) was added pentafluorobenzenesulfonyl chloride (0.99 g, 3.7 mmol). The solution was stirred at rt for 2 h. Saturated aqueous NaHCO$_3$ (12 mL) was added to the solution and the mixture was stirred at rt for 30 min. The organics were extracted with CH$_2$Cl$_2$ (75 mL) and washed with 1 M HCl (2×25 mL), saturated aqueous NaHCO$_3$ (1×25 mL) and saturated aqueous NaCl (1×25 mL). The organics were dried over Na$_2$SO$_4$ and concentrated to give a crude mixture. Silica gel chromatography with ethyl acetate in hexanes yielded the desired product (2.1 g, 81%). $^1$H NMR (400 MHz CDCl$_3$) δ 4.42 (t, 2H, J=7.3 Hz), 3.13 (s, 3H), 1.97 (t, 2H, J=7.4 Hz), 1.17 (s, 6H); $^{19}$F NMR (400 MHz CDCl$_3$) δ −137.9 (m, 2H), −146.65 (m, 1H), −161.01 (m, 2H). Anal. Calcd. For C$_{12}$H$_{13}$F$_5$O$_4$S: C, 41.38; H, 3.76. Found: C, 41.37; H, 3.77.

3-Hydroxybutyl 2-(trifluoromethyl)benzenesulfonate

To a solution of 1,3-butane diol (2.18 g, 24 mmol) and TEA (1.64 g, 16 mmol) in CH$_2$Cl$_2$ (15 mL) at 0° C. was added o-(trifluoromethyl)benzenesulfonyl chloride (2 g, 8 mmol) dissolved in CH$_2$Cl$_2$ (20 mL). The solution was stirred at 0° C. for 2 h. Saturated aqueous NaHCO$_3$ (15 mL) was added to the solution and mixture was stirred at rt for 45 min. The organics were extracted with CH$_2$Cl$_2$ (150 mL) and washed with 0.5 M HCl (2×80 mL) and saturated aqueous NaCl (1×50 mL). The organics were dried over Na$_2$SO$_4$ and concentrated to give a crude mixture. Silica gel chromatography (50% ethyl acetate in hexanes) yielded the desired product (2 g, 84%). $^1$H NMR (400 MHz CDCl$_3$) δ 8.23 (m, 1H), 7.92 (m, 1H), 7.74 (m, 2H), 4.34 (m, 1H), 4.24 (m, 1H), 3.95 (m, 1H), 1.89 (m, 1H), 1.73 (m, 1H), 1.20 (d, 3H, J=6.3 Hz). Anal. Calcd. For C$_{11}$H$_{13}$F$_3$O$_4$S: C, 44.29; H, 4.39. Found: C, 44.29; H, 4.28.

3-Hydroxybutyl 2,3,4,5,6-pentafluorobenzenesulfonate

To a solution of 1,3-butane diol (0.9 g, 10 mmol) and TEA (0.61 g, 6 mmol) in CH$_2$Cl$_2$ (4 mL) at 0° C. was added pentafluorobenzenesulfonyl chloride (0.53 g, 2 mmol) dissolved in CH$_2$Cl$_2$ (4 mL). The solution was stirred for 6 h over which time the solution slowly warmed to rt. Saturated aqueous NaHCO$_3$ (25 mL) was added to the solution and the mixture was stirred at rt for 30 min. The organics were extracted with CH$_2$Cl$_2$ (50 mL) and washed with 0.5 M HCl (3×20 mL), saturated aqueous NaHCO$_3$ (1×20 mL) and saturated aqueous NaCl (1×20 mL). The organics were dried over Na$_2$SO$_4$ and concentrated to give a crude mixture. Silica gel chromatography with ethyl acetate in hexanes yielded the desired product (0.26 g, 40%). $^1$H NMR (400 MHz CDCl$_3$) δ 4.62 (m, 2H), 4.13 (m, 1H), 2.11 (m, 1H), 1.94 (m, 1H), 1.40 (d, 3H, J=6.2 Hz). Anal. Calcd. For C$_{10}$H$_9$F$_5$O$_4$S: C, 37.51; H, 2.83. Found: C, 37.70; H, 2.93.

3-Methoxybutyl 2-(trifluoromethyl)benzenesulfonate

To a solution of 3-methoxybutane-1-ol (0.63 g, 6.0 mmol) and TEA (0.42 g, 4.1 mmol), in CH$_2$Cl$_2$ (5 mL) was added o-(trifluoromethyl)benzenesulfonyl chloride (0.50 g, 2.0 mmol). The solution was stirred at rt for 2 h. The reaction mixture was diluted with CH$_2$Cl$_2$ (15 mL) and washed with 1 M HCl (3×15 mL), saturated aqueous NaHCO$_3$ (1×15 mL) and saturated aqueous NaCl (1×15 mL). The organics were dried over Na$_2$SO$_4$ and concentrated to give a crude mixture. Silica gel chromatography with ethyl acetate in hexanes yielded the desired product (0.34 g, 50%). $^1$H NMR (400 MHz CDCl$_3$) δ 8.23 (m, 1H), 7.91 (m, 1H), 7.75 (m, 2H), 4.24 (m, 2H), 3.40 (m, 1H), 3.21 (s, 3H), 1.80 (m, 2H), 1.10 (d, 3H, J=6.2 Hz). Anal. Calcd. For C$_{12}$H$_{15}$F$_3$O$_4$S: C, 46.15; H, 4.84. Found: C, 46.30; H, 4.88.

3-Methoxybutyl 2,3,4,5,6-pentafluorobenzenesulfonate

To a solution of 3-methoxybutane-1-ol (0.78 g, 7.5 mmol) and TEA (0.388 g, 3.8 mmol), in CH$_2$Cl$_2$ (15 mL) was added pentafluorobenzenesulfonyl chloride (0.79 g, 3.0 mmol). The solution was stirred at rt for 4 h. Saturated aqueous NaHCO$_3$ (10 mL) was added to the solution and the mixture was stirred at rt for 30 min. The organics were extracted with CH$_2$Cl$_2$ (30 mL) and washed with 0.5 M HCl (2×20 mL) and saturated aqueous NaCl (1×20 mL). The organics were dried over Na$_2$SO$_4$ and concentrated to give a crude mixture. Silica gel chromatography (15% ethyl acetate in hexanes) yielded the desired product (0.39 g, 36%). $^1$H NMR (400 MHz CDCl$_3$) δ 4.40 (m, 2H), 3.45 (m, 1H), 3.26 (s, 3H), 1.87 (m, 2H), 1.15 (d, 3H, J=6.1 Hz). Anal. Calcd. For C$_{11}$H$_{11}$F$_5$O$_4$S: C, 39.53; H, 3.32. Found: C, 39.83; H, 3.45.

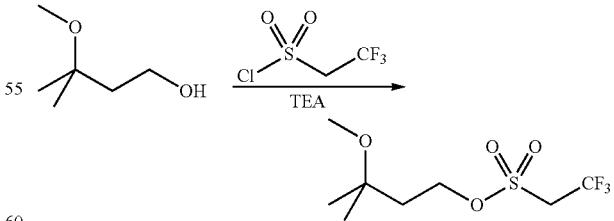

3-methoxy-3-methylbutyl 2,2,2-trifluoroethanesulfonate

To a solution of 3-methoxy-3-methylbutane-1-ol (0.4 g, 3.4 mmol) and TEA (0.2 g, 2 mmol) in CH$_2$Cl$_2$ (6 mL) was added 2,2,2-trifluoroethanesulfonyl chloride (0.12 g, 0.66 mmol). The solution was stirred at rt for 1 h. The organics were extracted with CH$_2$Cl$_2$ (25 mL) and washed with 0.1 M HCl (3×20 mL), saturated aqueous NaHCO$_3$ (1×20 mL) and saturated aqueous NaCl (1×20 mL). The organics were dried over Na$_2$SO$_4$ and concentrated to give a crude mixture. Silica gel chromatography with ethyl acetate in hexanes yielded the desired product as an oil (0.086 g, 50%). $^1$H NMR (400 MHz CDCl$_3$) δ 4.41 (t, 2H, J=7.3 Hz), 3.87 (q, 2H, J=8.8 Hz), 3.14 (s, 3H), 1.94 (t, 2H, J=7.3), 1.16 (s, 6H).

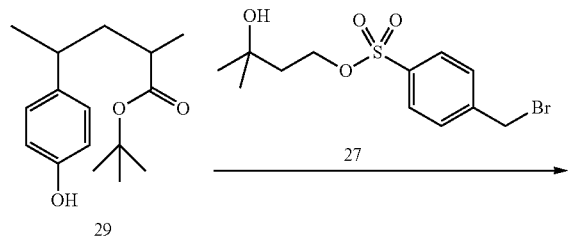

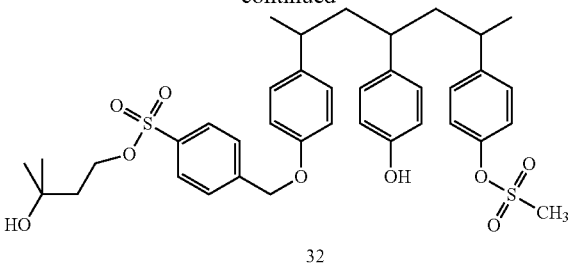

AA Bound Negative Resist Polymer (32)

The 3-hydroxy-3-methylbutyl-4-(methyl)benzene sulfonate bounded polymer is made in the following manner. The co-polymer(31) is reacted with 0.1 equivalents of 3-hydroxy-3-methylbutyl 4-(bromomethyl)benzenesulfonate(27) in presence of potassium carbonate at 50° C. to yield the acid amplifier bounded polymer.

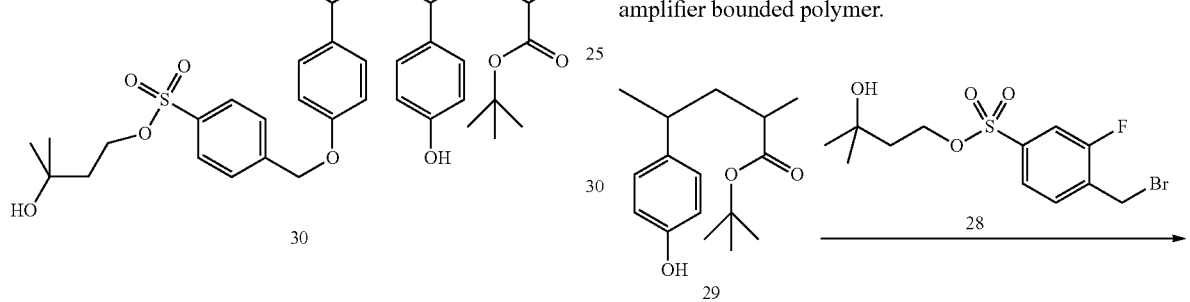

AA Bound Positive Resist Polymer (30)

To a solution of ter-polymer (29) (2.00 g, 12.151 mmol) dissolved in 20 mL of acetonitrile, anhydrous potassium carbonate (0.420 g, 3.038 mmol) was added and stirred for 10 mins at 20° C. 3-hydroxy-3-methylbutyl 4-(bromomethyl) benzenesulfonate(27) (0.41 g, 1.215 mmol) was added then added and the reaction mixture was heated to 50° C. and stirred overnight. Upon completion, the reaction mixture was quenched with acetic acid (ca. 0.75 mL, 1 N) to pH 5-6 and taken into ethyl acetate (100 mL). The organic layer was washed with brine (3×25 mL) and dried over Na$_2$SO$_4$. The solvent was then reduced to a minimum volume and the polymer was precipitated out with methylene chloride. The polymer was filtered and washed with methylene chloride to get the pure polymer (1.145 g). $^1$H NMR (DMSO-d$_6$): δ 0.52-2.43 (br. m, 20H), 4.06 (br. s, 2H CH$_2$), 4.35 (br. s., 1H, OH), 5.03 (br.s, 2H, Ph-CH$_2$-Ph), 6.59 (br.s., 4H), 7.42 (br.s., 2H, Ph), 7.67 (br.s., 2H, Ph), 9.08 (br.s., polymeric OH).

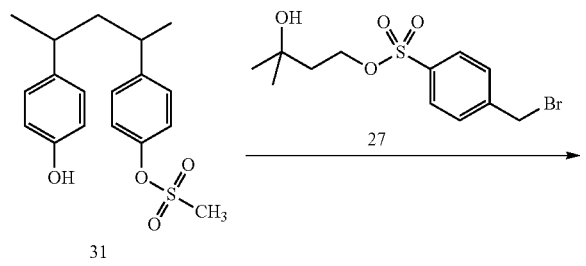

AA Bound Positive Resist Polymer (33)

The 3-hydroxy-3-methylbutyl-4-(methyl)-3-fluorobenzene sulfonate bounded polymer is made in the following manner. The co-polymer (29) is reacted with 0.1 equivalents of 3-hydroxy-3-methylbutyl 4-(bromomethyl)-3-fluorobenzenesulfonate(28) in presence of potassium carbonate at 50° C. to yield the acid amplifier bounded polymer.

LITHOGRAPHY

Example 1

Resist 1 was prepared by mixing the specified component with the amounts expressed as a percent by weight based on the total solids of the composition.

| Component | Amount |
| --- | --- |
| Resin | |
| Terpolymer (65% hydroxystyrene, 20% Styrene, 15% tert-butylacrylate) | 4.425 |
| Photoacid Gernerator | |
| Di-t-butylphenyl iodonium nonaflate | 0.375 |
| Base Additive | |
| Tetrabutyl ammonium lactate | 0.025 |
| Acid Amplifier | |
| 2-methyl-4-(tosyloxy) Butan-2-yl acetate | 0.100 |
| Solvents | |
| Ethyl lactate | 47.5 |
| Propylene Glycol Methyl Ether Acetate | 47.5 |

Example 2

Resists 2-12 were prepared in the same fashion as resist 1 except that the type of acid amplifier added to the resist and the amount of acid amplifier were varied as shown in the table. Resists 1-4 contained an equimolar amount of the different acid amplifiers. Resists 6 and 7 contained an equal amount of acid amplifier greater than that of resists 1-4. Resists 7-10 contained increasing amounts of the same acid amplifier.

| Ex No. | PAG | Acid Amplifier | Amount Added | Amount of Base |
| --- | --- | --- | --- | --- |
| 1 | Yes | 2-methyl-4-(tosyloxy) Butan-2-yl acetate | 0.1 | 0.025 |
| 2 | Yes | 2-methyl-4-(4-(trifluoromethyl) Phenylsulfonyloxy)butan-2-yl acetate | 0.106 | 0.025 |
| 3 | Yes | 3-hydroxy-3-methylbutyl-4-methylbenzenesulfonate | 0.0763 | 0.025 |
| 4 | Yes | 3-hydroxy-3-methylbutyl 4-(triflouromethyl)benzenesulfonate | 0.0937 | 0.025 |
| 5 | Yes | None Added | — | 0.025 |
| 6 | No | 2-methyl-4-(4-(trifluoromethyl) Phenylsulfonyloxy)butan-2-yl acetate | 0.213 | 0.025 |
| 7 | Yes | 2-methyl-4-(4-(trifluoromethyl) Phenylsulfonyloxy)butan-2-yl acetate | 0.213 | 0.025 |
| 8 | Yes | 3-hydroxybutyl-4-(trifluoromethyl)benzenesulfonate | 0.045 | 0.05 |
| 9 | Yes | 3-hydroxybuty1-4-(trifluoromethyl)benzenesulfonate | 0.088 | 0.05 |
| 10 | Yes | 3-hydroxybuty1-4-(trifluoromethyl)benzenesulfonate | 0.173 | 0.05 |
| 11 | Yes | 3-hydroxybuty1-4-(trifluoromethyl)benzenesulfonate | 0.334 | 0.05 |
| 12 | Yes | None Added | — | 0.05 |

Example 3

The resists 1 through 5 were spin coated on HMDS primed silicon wafers to obtain a nominal film thickness of 1250 Å and soft baked on a hotplate at 110° C. for 60 seconds. The resists were then exposed to EUV radiation up to a dose of 10 mJ/cm$^2$ on an exposure tool having a numerical aperture of 0.3.

A 10×10 open frame exposure matrix was used to determine the clearing dose (Eo) of the resists. The exposed films were then post exposure baked on a hot plate at 110° C. for 90 seconds. The resist films were then subsequently developed for 45 seconds using MF-26A (0.26N) standard developer.

Resists 1-4 which contained acid amplifiers all exhibited a lower Eo than that of resist 5, which did not contain an acid amplifier. Also, resists that contained a fluorinated acid amplifier had a lower Eo than that of a similar base molecule which did not contain a fluorinated acid. Thirdly, resists that contained acid amplifiers with alcohol triggers exhibited lower Eo's than the resists that contained acid amplifiers with acetate triggers.

Example 4

Resists 5-7 were spin coated, exposed up to a dose of 20 mJ/cm$^2$, and processed in the same manner described in example 3.

The resist that contained an acid amplifier but did not contain a photoacid generator did not show any change in the dissolution rate of the film up to a dose of 20 mJ/cm$^2$. Resist 7 which contained an equimolar amount of the same acid amplifier and included a photoacid generator showed a significantly lower Eo than the resist which contained only photoacid generator.

Example 5

The resists 1 through 5 were spin coated on HMDS primed silicon wafers to obtain a nominal film thickness of 1250 Å and soft baked on a hotplate at 110° C. for 60 seconds. The resists were then exposed to EUV radiation at doses not greater than 20 mJ/cm$^2$ on an exposure tool which has a numerical aperture of 0.3.

Resist Images were obtained by exposing the resists using a 7×13 focus exposure matrix. The exposed films were then post exposure baked on a hot plate at 110° C. for 90 seconds and subsequently developed for 45 seconds using MF-26A (0.26N) standard developer.

The through dose CD performance was then analyzed for 60 nm dense lines. The resists that contained fluorinated acid amplifiers precursors showed better exposure latitude performance and lower sizing doses than their non-fluorinated acid amplifier precursor counterparts. The resists that contained acid amplifiers with alcohol triggers showed lower sizing doses but significantly less exposure latitudes than the resists containing acetate triggers for both acid amplifier acid precursors.

| Resist No. | Eo (mJ/cm$^2$) | Esize (mJ/cm$^2$) | Exposure Latitude (%) |
|---|---|---|---|
| 1 | 4.0 | 5.4 | 18.6 |
| 2 | 3.7 | 4.9 | 22.7 |
| 3 | 2.8 | 3.5 | 6.1 |
| 4 | 2.6 | 1.9 | 8.0 |
| 5 | 4.4 | 7.6 | 21.5 |

Example 6

Resist Images were obtained by exposing resists 8-12 in the same manner as described in example 5. The through dose CD performance was then analyzed for 50 nm dense lines.

Increased amounts of acid amplifier added to the resist caused the sizing dose to decrease. Resists 8 and 9, which contained relatively smaller amounts of acid amplifier, did not show a change in the exposure latitude when compared to the resist that did not contain an acid amplifier. Resists 10 and 11, which contained larger amounts of acid amplifier, showed a decrease in exposure latitude when compared to the other resists.

| Resist No. | Esize (mJ/cm$^2$) | Exposure Latitude (%) |
|---|---|---|
| 8 | 12.5 | 23.4 |
| 9 | 11.4 | 22.6 |
| 10 | 8.1 | 15.6 |
| 11 | 5.8 | 16.0 |
| 12 | 14.5 | 21.4 |

Skilled artisans will appreciate variations which may be employed to obtain ethers, amines, thiols, thiol ethers and the like, rather than the alcohols or acetates depicted. It will also be appreciated that the alcohols may be esterified with a polymer, such as the photoresist polymer. In some cases, it is expected that this will result in higher concentrations of the acid amplifiers in the resists than would otherwise be achievable, without significant derogation from other resist properties. Furthermore, depending on the choice of acid amplifier, attachment to the polymer may be used to affect the solubility of the polymer, i.e. to create a "solubility switch".

The invention has been described in detail with particular reference to some embodiments thereof, but it will be understood by those skilled in the art that variations and modifications can be effected within the spirit and scope of the invention.

The invention claimed is:

1. A compound of formula

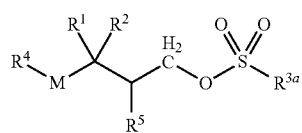

wherein

M is —O—, —S— or —NR$^9$—;

R$^1$ is chosen from (C$_1$-C$_8$)saturated hydrocarbon; (C$_1$-C$_8$) saturated hydrocarbon substituted with halogen, cyano or nitro; (C$_1$-C$_8$)silaalkane and optionally substituted phenyl;

R$^2$ is chosen from H, (C$_1$-C$_6$) hydrocarbon and (C$_1$-C$_6$) hydrocarbon substituted with nitro or cyano, or taken together with the carbon to which they are attached, R$^1$ and R$^2$ form a (C$_3$-C$_6$) hydrocarbon ring;

R$^{3a}$ is chosen from
(a) —C$_n$H$_m$F$_p$ wherein n is 2-8, m is 0-16, p is 1-17 and the sum of m plus p is 2n+1;
(b) —CH$_2$C(=O)-Q;
(c) —CF$_2$C(=O)-Q;
(d)

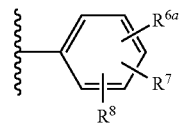

(e) —(CH$_2$)$_q$Cl, wherein q is an integer from 1 to 8; and
(f) when none of R$^1$, R$^2$ and R$^5$ contains or forms a carbocycle, R$^{3a}$ may additionally be

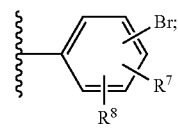

R$^4$ is chosen from H, (C$_1$-C$_6$)alkyl, —C(=O)(C$_1$-C$_6$) alkyl, —C(=O)(C$_1$-C$_6$)alkenyl, —C(=O)(C$_1$-C$_6$)haloalkyl, benzyl, substituted benzyl, —C(=O)phenyl, —C(=O)substituted phenyl, —SO$_2$-phenyl and —SO$_2$ (substituted)phenyl;

R$^5$ is chosen from H, (C$_1$-C$_6$) hydrocarbon, nitro, cyano, (C$_1$-C$_6$) hydrocarbon substituted with nitro or cyano, and (C$_1$-C$_6$)silaalkane, or together with the carbons to which they are attached, R$^1$ and R$^5$ form a (C$_3$-C$_6$) hydrocarbon ring;

R$^{6a}$ is chosen from —CF$_3$, —OCH$_3$, —NO$_2$, F, Cl, —CH$_2$Br, —CH=CH$_2$, —OCH$_2$CH$_2$Br, —CH$_2$-Q, —O-Q, —OCH$_2$CH$_2$-Q, —OCH$_2$CH$_2$O-Q, and —CH (Q)CH$_2$-Q;

R$^7$ is chosen from one to three instances of H, —CF$_3$, —OCH$_3$, —CH$_3$, —NO$_2$, F, Br, and Cl;

R$^8$ is chosen from H, —CF$_3$, —OCH$_3$, —CH$_3$, —NO$_2$, F, Br, and Cl;

R$^9$ is chosen from H, (C$_1$-C$_6$)alkyl, —C(=O)(C$_1$-C$_6$)alkyl and phenyl, or taken together with R$^4$, R$^9$ together with the nitrogen to which they are attached may form a nitrogen heterocycle, with the proviso that when R$^4$ and R$^9$ are attached to nitrogen, one of R$^4$ and R$^9$ must be an acyl, and when R$^4$ and R$^9$ together with the nitrogen to which they are attached form a heterocycle, the heterocyle must contain one or two α-oxo substituents; and Q is a polymer or oligomer;

with the provisos that,
(a) when R$^4$, R$^7$ and R$^8$ are hydrogen, R$^2$ is n-propyl and R$^5$ is ethyl, R$^{6a}$ cannot be Cl in the para position; and
(b) when R$^1$, R$^2$ and R$^5$ are hydrogen and R$^4$ is ethyl, R$^3$ cannot be Br in the para position.

2. A compound according to claim 1 wherein R$^{3a}$ is —C$_n$F$_{2n+1}$.

3. A compound according to claim 1 wherein $R^{3a}$ is

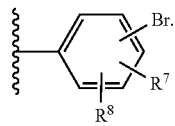

4. A compound according to claim 1 wherein $R^{3a}$ is

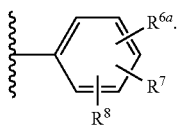

5. A compound according to claim 4 wherein $R^{6a}$ is $CF_3$.
6. A compound according to claim 4 wherein $R^{6a}$ is chosen from $-CH_2Br$, $-CH=CH_2$, and $-OCH_2CH_2Br$.
7. A compound according to claim 4 wherein $R^{6a}$ is chosen from $-CH_2-Q$, $-O-Q$, $-OCH_2CH_2-Q$, $-OCH_2CH_2O-Q$ and $-CH(O)CH_2-Q$.
8. A compound according to claim 1 wherein
  $R^1$ is chosen from methyl, cyclopropyl, trimethylsilylmethyl, phenyl, nitrophenyl, nitromethyl, cyanomethyl; and
  $R^2$ is chosen from H, propenyl, propynyl, dimethylbutynyl and methyl.
9. A compound according to claim 1 wherein
  $R^1$ and $R^2$ taken together form a cyclobuty, cyclopentyl or cyclohexyl ring.
10. A compound according to claim 1 wherein $R^5$ is chosen from H, $NO_2$, CN, $SiMe_3$, and methyl.
11. A compound according to claim 1 wherein
  $R^1$ and $R^5$ taken together form a cyclopentyl or cyclohexyl ring.
12. A compound according to claim 1 wherein M is oxygen.
13. A compound according to claim 12 wherein $R^4$ is chosen from H, methyl, ethyl, isopropyl, t-butyl, benzyl, acetyl, chloroacetyl, dichloroacetyl, trichloroacetyl, benzoyl, 4-(trifluoromethyl)benzoyl, 4-carboxybenzoyl, 4-nitrobenzoyl, 4-methoxybenzoyl, benzenesulfonyl, 4-(trifluoromethyl)benzenesulfonyl, 4-nitrobenzenesulfonyl, 4-carboxybenzenesulfonyl and 4-methoxybenzenesulfonyl.
14. A compound according to claim 1 wherein
  M is $-NR^9-$.
15. A compound according to claim 14 wherein $R^4$ is chosen from H, methyl, ethyl, isopropyl, t-butyl and benzyl.
16. A compound according to claim 14 wherein $R^9$ is acetyl.
17. A compound according to claim 14 wherein $R^4$, $R^9$ together with the nitrogen to which they are attached form a pyrrolidone, phthalimide, maleimide or succinimide.
18. A compound according to claim 1 wherein M is sulfur and $R^4$ is chosen from H, methyl, ethyl, isopropyl, t-butyl, benzyl, acetyl, chloroacetyl, dichloroacetyl, trichloroacetyl, benzoyl, 4-(trifluoromethyl)benzoyl, 4-nitrobenzoyl, 4-carboxybenzoyl and 4-methoxybenzoyl.
19. A photoresist composition comprising:
  (a) a photoresist polymer; and
  (b) a compound according to claim 1.
20. A photoresist substrate which is coated with a photoresist composition according to claim 19.

21. A method for preparing a substrate for photolithography, comprising coating said substrate with a composition according to claim 19.
22. A method for conducting photolithography on a substrate, comprising (a) providing a substrate, (b) coating said substrate with a composition according to claim 19, and (c) irradiating the coated substrate through a photomask.
23. A method according to claim 22, wherein said irradiation is conducted using electromagnetic radiation of wavelength 248 nm, 193 nm, 13.5 nm, or radiation from electron or ion beams.
24. A compound of formula

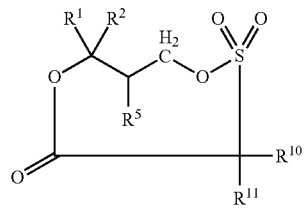

wherein
  $R^1$ is chosen from $(C_1-C_8)$saturated hydrocarbon; $(C_1-C_8)$ saturated hydrocarbon substituted with halogen, cyano or nitro; $(C_1-C_8)$silaalkane and optionally substituted phenyl;
  $R^2$ is chosen from H, $(C_1-C_6)$ hydrocarbon and $(C_1-C_6)$ hydrocarbon substituted with nitro or cyano, or taken together with the carbon to which they are attached, $R^1$ and $R^2$ form a $(C_3-C_6)$ hydrocarbon ring;
  $R^5$ is chosen from H, $(C_1-C_6)$ hydrocarbon, nitro, cyano, $(C_1-C_6)$ hydrocarbon substituted with nitro or cyano, and $(C_1-C_6)$silaalkane, or together with the carbons to which they are attached, $R^1$ and $R^5$ form a $(C_3-C_6)$ hydrocarbon ring;
  $R^{10}$ is chosen from H, F and $(C_1-C_6)$ hydrocarbon; and
  $R^{11}$ is chosen from H and F.
25. A compound of formula

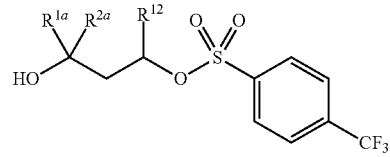

wherein
  $R^{1a}$, and $R^{12}$ are independently chosen from $(C_1-C_8)$saturated hydrocarbon; and
  $R^{2a}$ is chosen from H and $(C_1-C_6)$ hydrocarbon.
26. A compound according to claim 25 wherein all of $R^{1a}$, $R^{2a}$ and $R^{12}$ are methyl.
27. A composition for photolithography comprising:
  (a) a photolithographic polymer; and
  (b) a compound of formula

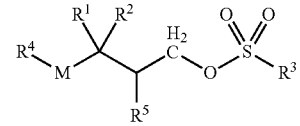

wherein
  M is $-O-$, $-S-$ or $-NR^9-$;
  $R^1$ is chosen from $(C_1-C_8)$saturated hydrocarbon; $(C_1-C_8)$ saturated hydrocarbon substituted with halogen, cyano or nitro; $(C_1-C_8)$silaalkane and optionally substituted phenyl;

$R^2$ is chosen from H, ($C_1$-$C_6$) hydrocarbon and ($C_1$-$C_6$) hydrocarbon substituted with nitro or cyano, or taken together with the carbon to which they are attached, $R^1$ and $R^2$ form a ($C_4$-$C_6$) hydrocarbon ring;

$R^3$ is chosen from
- (a) —$C_nH_mF_p$ wherein n is 1-8, m is 0-17, p is 0-17 and the sum of m plus p is 2n+1;
- (b) —$CH_2C(=O)$-Q;
- (c) —$CF_2C(=O)$-Q;
- (d)

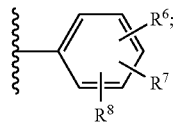

- (e) —$(CH_2)_qCl$, wherein q is an integer from 1 to 8;

$R^4$ is chosen from H, ($C_1$-$C_6$)alkyl, —$C(=O)(C_1$-$C_6)$alkyl, —$C(=O)(C_1$-$C_6)$alkenyl, —$C(=O)(C_1$-$C_6)$haloalkyl, benzyl, substituted benzyl, —$C(=O)$phenyl, —$C(=O)$substituted phenyl, —$SO_2$-phenyl and —$SO_2$(substituted)phenyl;

$R^5$ is chosen from H, ($C_1$-$C_6$) hydrocarbon, nitro, cyano, ($C_1$-$C_6$) hydrocarbon substituted with nitro or cyano, and ($C_1$-$C_6$)silaalkane, or together with the carbons to which they are attached, $R^1$ and $R^5$ form a ($C_4$-$C_6$) hydrocarbon ring;

$R^6$ is chosen from H, $CH_3$, —$CF_3$, —$OCH_3$, —$NO_2$, F, Br, Cl, —$CH_2Br$, —$CH=CH_2$, —$OCH_2CH_2Br$, —$CH_2$-Q, —O-Q, —$OCH_2CH_2$-Q, —$OCH_2CH_2$O-Q and —CH(O)$CH_2$-Q;

$R^7$ is chosen from one to three instances of H, —$CF_3$, —$OCH_3$, —$CH_3$, —$NO_2$, F, Br, and Cl;

$R^8$ is chosen from H, —$CF_3$, —$OCH_3$, —$CH_3$, —$NO_2$, F, Br, and Cl;

$R^9$ is chosen from H, ($C_1$-$C_6$)alkyl, —$C(=O)(C_1$-$C_6)$alkyl and phenyl, or taken together with $R^4$, $R^9$ together with the nitrogen to which they are attached may form a nitrogen heterocycle, with the proviso that when $R^4$ and $R^9$ are attached to nitrogen, one of $R^4$ and $R^9$ must be an acyl, and when $R^4$ and $R^9$ together with the nitrogen to which they are attached form a heterocycle, the heterocyle must contain one or two α-oxo substituents; and Q is a polymer or oligomer.

* * * * *